US008868160B2

(12) United States Patent
Kubo et al.

(10) Patent No.: US 8,868,160 B2
(45) Date of Patent: *Oct. 21, 2014

(54) MEDICAL APPARATUS

(75) Inventors: Kei Kubo, Hino (JP); Nobuyuki Doguchi, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/495,059

(22) Filed: Jun. 13, 2012

(65) Prior Publication Data

US 2012/0271128 A1    Oct. 25, 2012

Related U.S. Application Data

(63) Continuation of application No. PCT/JP2011/075687, filed on Nov. 8, 2011.

(30) Foreign Application Priority Data

Dec. 13, 2010   (JP) ................................. 2010-277340

(51) Int. Cl.
| | | |
|---|---|---|
| A61B 6/00 | (2006.01) | |
| A61B 1/00 | (2006.01) | |
| A61B 1/04 | (2006.01) | |
| A61B 1/06 | (2006.01) | |

(52) U.S. Cl.
CPC ............. *A61B 1/043* (2013.01); *A61B 1/00006* (2013.01); *A61B 1/041* (2013.01); *A61B 1/0661* (2013.01)
USPC .......................................... 600/476; 424/9.6

(58) Field of Classification Search
CPC ............ G01N 33/533; A61K 49/0032; A61K 49/0052; A61K 49/0034; A61M 5/16836; A61M 5/168; A61B 3/1241; A61B 1/00006; A61B 1/043; A61B 5/0071; A61B 5/0275; A61B 5/0661; A61B 5/043
USPC .............................. 424/9.6; 600/317, 312, 321
See application file for complete search history.

(56) References Cited

U.S. PATENT DOCUMENTS

| 5,971,918 A | 10/1999 | Zanger | |
|---|---|---|---|
| 7,966,051 B2 * | 6/2011 | Xie et al. ...................... | 600/317 |
| 2002/0099310 A1 | 7/2002 | Kimchy et al. | |
| 2006/0089554 A1 | 4/2006 | Ishihara et al. | |

(Continued)

FOREIGN PATENT DOCUMENTS

| JP | 10-113327 | 5/1998 |
|---|---|---|
| JP | 2004-521680 | 7/2004 |
| JP | 2006-061683 | 3/2006 |
| JP | 2006-122131 | 5/2006 |
| JP | 2006-194646 | 7/2006 |
| JP | 2007-125355 | 5/2007 |

(Continued)

*Primary Examiner* — Elmer Chao
(74) *Attorney, Agent, or Firm* — Scully, Scott, Murphy & Presser, PC

(57) ABSTRACT

A medical apparatus includes: a storing section in which information concerning a drug kinetics in a living body is stored in advance for each of plural kinds of fluorescent drugs; a processing section that acquires information concerning diagnosis start timing corresponding to a desired fluorescent drug based on information stored in the storing section, information concerning a target region to which the desired fluorescent drug is administered, information concerning a method of administering the desired fluorescent drug to the target region, and information indicating start of the administration of the desired fluorescent drug; and a light source control section that controls radiation of excitation light for exciting the desired fluorescent drug to a stop state until the diagnosis start timing is reached and controls, at and after the diagnosis start timing, the radiation of the excitation light to a state in which the excitation light can be radiated.

8 Claims, 18 Drawing Sheets

(56) References Cited

U.S. PATENT DOCUMENTS

2006/0188402 A1    8/2006   Xie et al.
2011/0104056 A1*   5/2011   Hara et al. .................. 424/1.65

FOREIGN PATENT DOCUMENTS

| JP | 2007-303990 | 11/2007 |
|---|---|---|
| WO | WO 02/058531 A2 | 8/2002 |

* cited by examiner

FIG.19
FLUORESCENT DRUG A
| ADMINISTERING METHOD \ TARGET REGION | LARGE INTESTINE | STOMACH | ESOPHAGUS | ... |
|---|---|---|---|---|
| INTRAVENOUS INJECTION | DRUG KINETICS A01 | DRUG KINETICS A02 | DRUG KINETICS A03 | ... |
| SPRAY | DRUG KINETICS A11 | DRUG KINETICS A12 | DRUG KINETICS A13 | ... |
| ⋮ | ⋮ | ⋮ | ⋮ | |
FIG.20
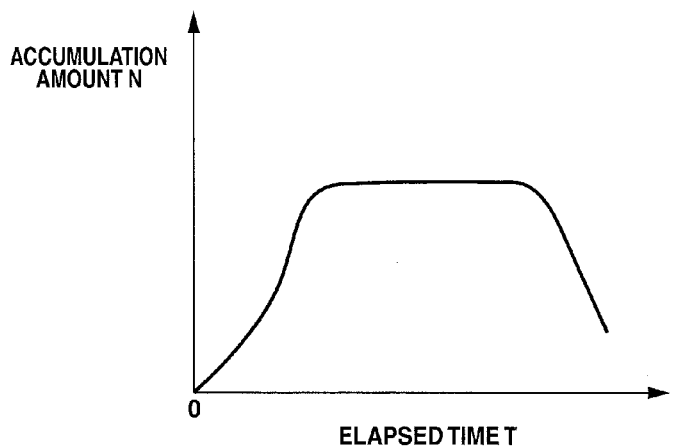
FIG.21
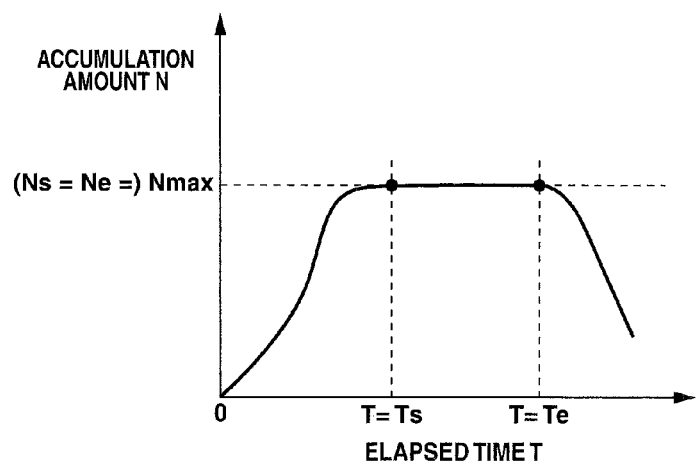

MEDICAL APPARATUS

CROSS REFERENCE TO RELATED APPLICATION

This application is a continuation application of PCT/JP2011/075687 filed on Nov. 8, 2011 and claims benefit of Japanese Application No. 2010-277340 filed in Japan on Dec. 13, 2010, the entire contents of which are incorporated herein by this reference.

BACKGROUND OF THE INVENTION

1. Field of the Invention

The present invention relates to a medical apparatus and, more particularly, to a medical apparatus that can perform observation based on fluorescence from a florescent drug.

2. Description of the Related Art

In recent years, a cancer diagnosis technology employing a molecular target drug has started to attract attention. Specifically, for example, in recent years, a method of, after administering a fluorescent drug (a fluorescent probe) that targets biological protein specifically developing in a cancer cell to a living body, discriminating presence or absence of cancer based on fluorescence in a target region of the living body has been studied. Such a method is useful in early detection of cancer in the digestive tract field.

As an applied method of the method explained above, a method of, after administering plural kinds of fluorescent drugs having different fluorescence wavelengths to a living body, complexly observing, based on plural kinds of fluorescence in a target region of the living body, development states of plural kinds of biological protein corresponding to the plural kinds of fluorescent drugs has been proposed. Such a method is considered to be useful in, for example, estimation of a stage of cancer, prediction of an invasion risk of cancer, and prediction of a spread risk of cancer.

For example, Japanese Patent Application Laid-Open Publication No. 2006-61683 discloses an endoscope apparatus including a laser beam source that generates excitation light, an endoscope scope including a radiating section of the excitation light at a distal end portion thereof, an intensifier equipped CCD that detects fluorescence generated in an object to be examined by the excitation light, fluorescent image generating means for generating a fluorescent image signal based on a fluorescent signal from the intensifier equipped CCD, distance measuring means for generating a distance signal equivalent to a distance between the radiating section and the object to be examined, and fluorescence intensity calculating means for correcting the fluorescent signal with the distance signal and calculating a fluorescence intensity not affected by fluctuation in the distance. In the configuration of the endoscope apparatus, the fluorescence intensity calculating means includes time-after-drug-administration correcting means for correcting the fluorescent signal or the fluorescent image signal based on elapsed time after the administration of the fluorescent drug.

With the configuration disclosed in Japanese Patent Application Laid-Open Publication No. 2006-61683, even before influence of the administered fluorescent drug spreads all over the object to be examined, a fluorescent image can be corrected to a state after the influence of the fluorescent drug spreads all over the object to be examined.

SUMMARY OF THE INVENTION

A medical apparatus according to an aspect of the present invention includes: a storing section in which information concerning a drug kinetics in a living body is stored in advance for each of plural kinds of fluorescent drugs; a processing section that acquires information concerning diagnosis start timing corresponding to a desired fluorescent drug based on information stored in the storing section, information concerning a target region of an object to be examined to which the desired fluorescent drug is administered, information concerning a method of administering the desired fluorescent drug to the target region, and information indicating start of the administration of the desired fluorescent drug; and a light source control section that controls radiation of excitation light for exciting the desired fluorescent drug to a stop state at least until the diagnosis start timing is reached and controls, at and after the diagnosis start timing, the radiation of the excitation light to a state in which the excitation light can be radiated.

BRIEF DESCRIPTION OF THE DRAWINGS

FIG. 19 is a diagram showing an example of table data used in selecting a drug kinetics of a fluorescent drug;

FIG. 20 is a graph showing an example of a drug kinetics selected out of the table data;

FIG. 21 is graph showing an example of diagnosis start time and diagnosis end time acquired when the drug kinetics shown in FIG. 20 is selected;

DETAILED DESCRIPTION OF THE PREFERRED EMBODIMENTS

Embodiments of the present invention are explained below with reference to the accompanying drawings.

First Embodiment

FIGS. 1 to 26 relate to a first embodiment of the present invention.

Figure 1:
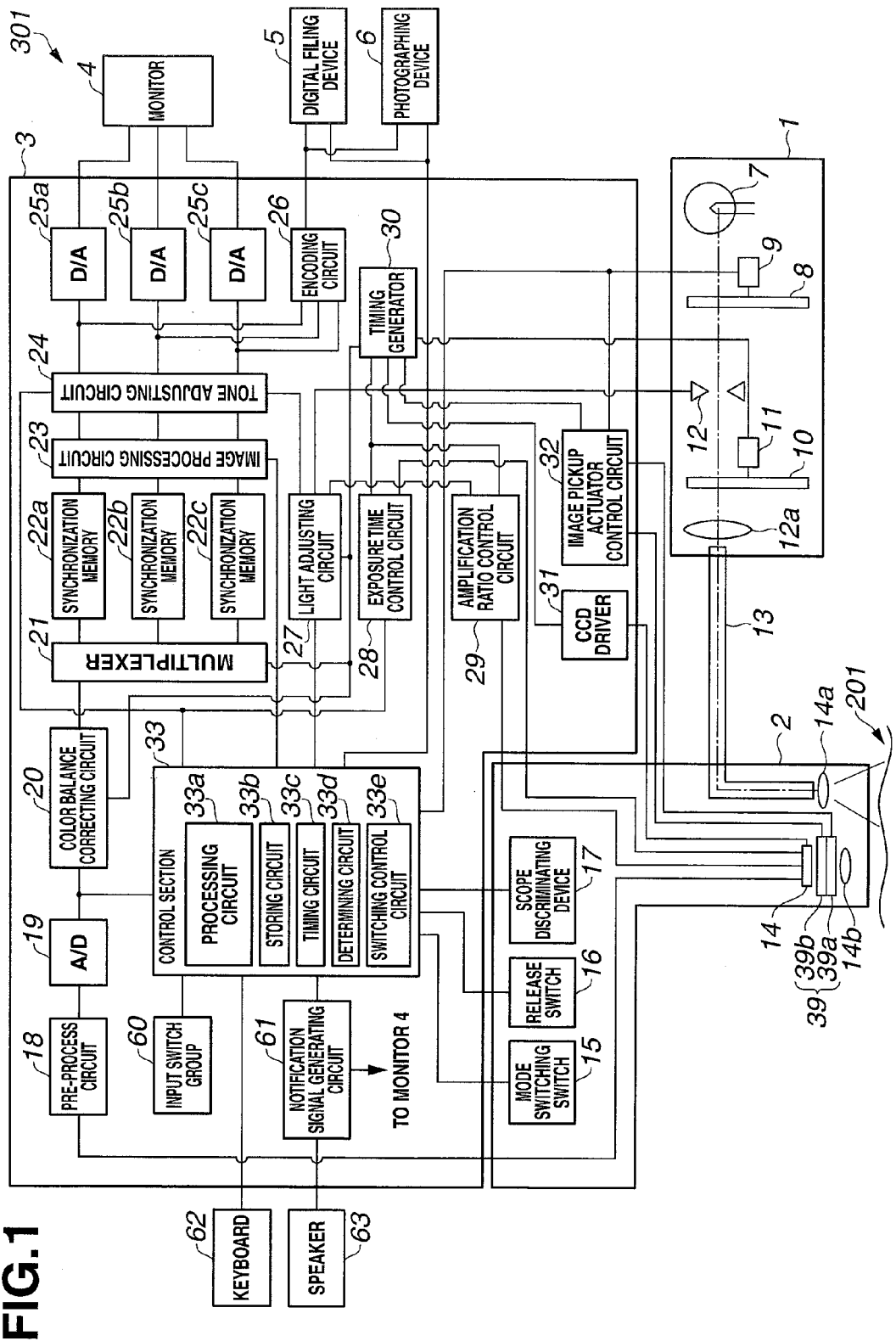
FIG. 1 is a diagram showing a configuration of a main part of an endoscope system according to a first embodiment of the present invention.

FIG. 1 is a diagram showing a configuration of a main part of an endoscope system according to a first embodiment of the present invention.

An endoscope system 301 includes, as shown in FIG. 1, a scope 2 that can be inserted into the body cavity of a subject and picks up an image of an observation target region 201 in the body cavity and outputs an image pickup signal, a light source device 1 that supplies illumination light for illuminating the observation target region 201 to be observed by the scope 2, a processor 3 that applies various kinds of signal processings to the image pickup signal outputted from the scope 2 and outputs the image pickup signal, a monitor 4 that displays an image corresponding to the output signal from the processor 3, a digital filing device 5 that records the image corresponding to the output signal from the processor 3, a photographing device 6 that photographs the image corresponding to the output signal from the processor 3, a keyboard 62 that can output a signal corresponding to key operation such as input operation of a character string to the processor 3, and a speaker 63 that emits sound corresponding to the output signal from the processor 3. A light guide 13 that transmits the illumination light, which is supplied from the light source device 1, to a distal end portion of the scope 2 is inserted through an inside of the scope 2.

The scope 2 includes, at the distal end portion, an illumination optical system 14a that emits the illumination light, which is transmitted by the light guide 13, to the observation target region 201, an object optical system 14b that forms an image of return light from the observation target region 201 illuminated by the illumination light, a monochrome-type CCD 14, an image pickup surface of which is arranged in an image-forming position of the object optical system 14b, and an image pickup actuator 39 arranged on an optical path between the object optical system 14b and the CCD 14. Further, the scope 2 includes a mode switching switch 15 with which operation related to switching of an observation mode of the endoscope system 301 is possible, a release switch 16 with which operation related to acquisition of a still image of the observation target region 201 is possible, and a scope discriminating device 17 in which peculiar discrimination information corresponding to a type or the like of the scope 2 is stored.

The CCD 14 is driven according to control by the processor 3 and applies photoelectric conversion to return light from the observation target region 201, which is focused on the image pickup surface, to thereby generate an image pickup signal and output the image pickup signal to the processor 3. A not-shown electronic shutter that can adjust exposure time and readout time according to the control by the processor 3 is provided in the CCD 14 in this embodiment. Further, a not-shown charge amplifying device is provided in the CCD 14 according to this embodiment.

Figure 2:
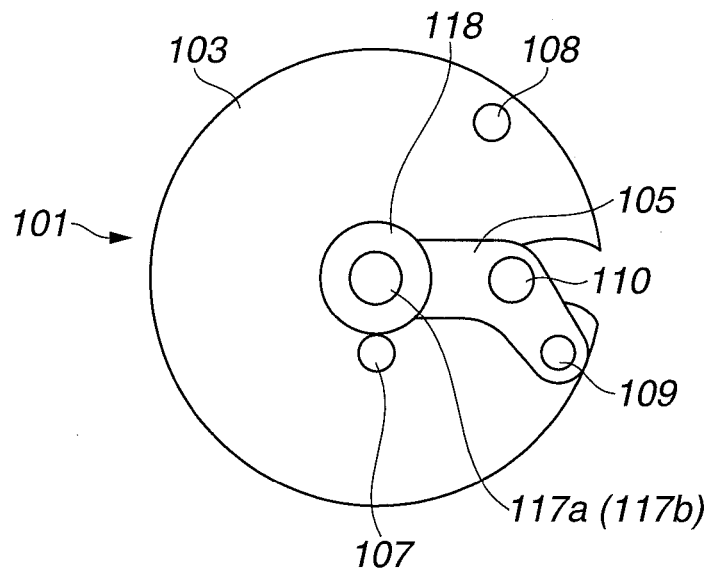
FIG. 2 is a diagram showing a state in which an optical filter is interposed on an optical path in a filter switching mechanism of an image pickup actuator.
Figure 3:
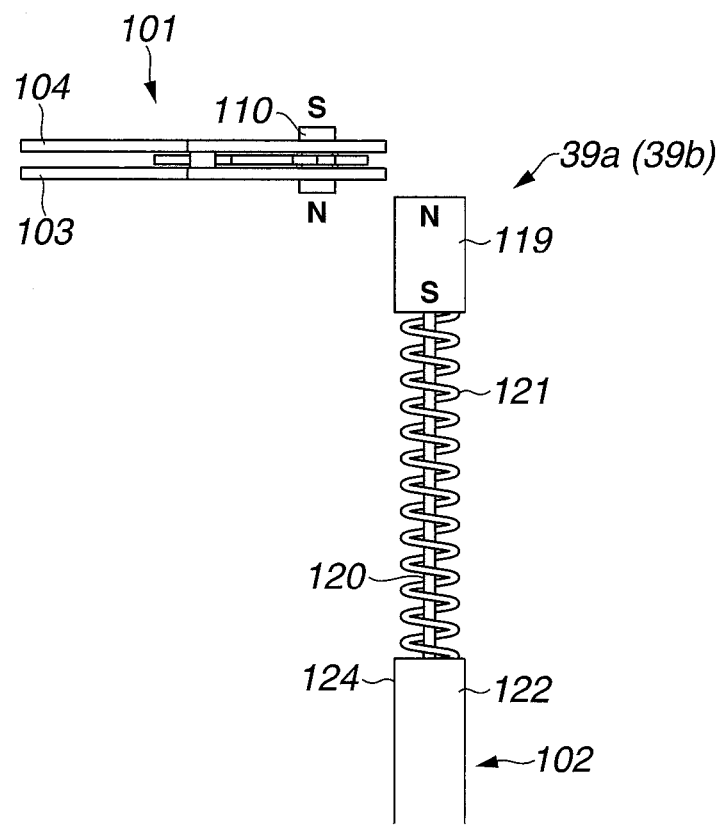
FIG. 3 is a diagram showing a state during energization of a magnet displacement device in setting the filter switching mechanism to the state shown in FIG. 2.
Figure 4:
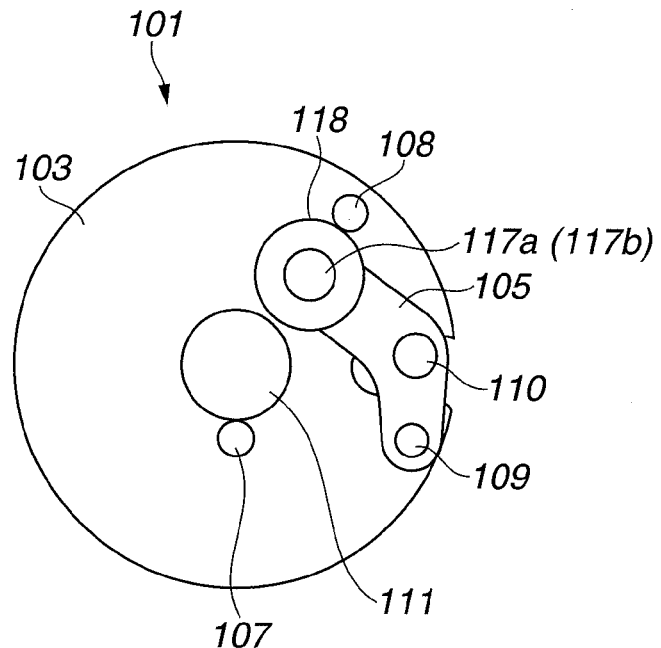
FIG. 4 is a diagram showing a state in which the optical filter is retracted from the optical path in the filter switching mechanism of the image pickup actuator.
Figure 5:
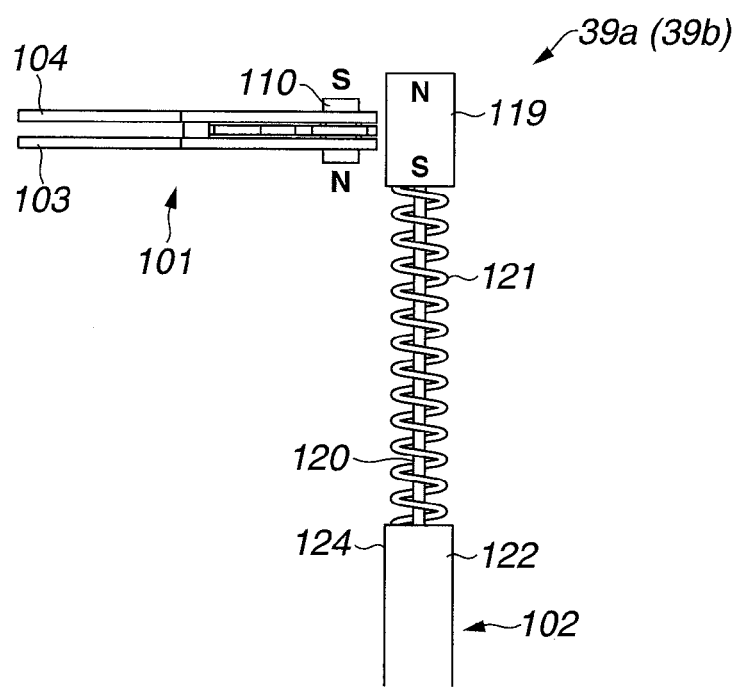
FIG. 5 is a diagram showing a state during non-energization of the magnet displacement device in setting the filter switching mechanism to the state shown in FIG. 4.

A detailed configuration of the image pickup actuator 39 is explained here. FIG. 2 is a diagram showing a state in which an optical filter is interposed on an optical path in a filter switching mechanism of the image pickup actuator. FIG. 3 is a diagram showing a state during energization of a magnet displacement device in setting the filter switching mechanism to the state shown in FIG. 2. FIG. 4 is a diagram showing a state in which the optical filter is retracted from the optical path in the filter switching mechanism of the image pickup actuator. FIG. 5 is a diagram showing a state during non-energization of the magnet displacement device in setting the filter switching mechanism to the state shown in FIG. 4.

A filter switching device 39a of the image pickup actuator 39 has a configuration capable of switching, according to the control by the processor 3, a first arrangement state (an interposed state) in which a filter that transmits only light in a predetermined wavelength band is interposed on an optical path extending from the object optical system 14b to the CCD 14 and a second arrangement state (a retraced state) in which the filter that transmits only the light in the predetermined wavelength band is retracted from the optical path extending from the object optical system 14b to the CCD 14.

Specifically, the filter switching device 39a of the image pickup actuator 39 has a configuration similar to the configuration of the light adjusting device described in Japanese Patent Application Laid-Open Publication No. 2009-8717. The filter switching device 39a includes a filter switching mechanism 101 and a magnet displacement device 102.

The filter switching mechanism 101 is formed to hold, between a lower board 103 and an upper board 104, a filter moving member 105, a closed-time stopper 107, and an open-time stopper 108.

One end of a shape memory alloy wire 120 is fixed to a magnet 119 of the magnet displacement device 102. A bias spring 121 and an insulative tube 122 are inserted through the shape memory alloy wire 120. On the other hand, the other end of the shape memory alloy wire 120 is fixed to a not-shown caulking member. The not-shown caulking member is also fixed at an end on an opposite side of the magnet 119 of the tube 122.

A rotating shaft 109 and a columnar magnet 110 are press-fit in the filter moving member 105. An optical filter section 118 including an optical filter 117a is provided in the filter moving member 105.

On the other hand, in the lower board 103, an optical opening 111, a rotating shaft insertion hole for inserting the rotating shaft 109, and a cutout for guide of the magnet 110 are formed. In the upper board 104, substantially like the lower board 103, an optical opening having a diameter same as or slightly larger than the optical opening 111, a rotating shaft insertion hole for inserting the rotating shaft 109, and a cutout for guide of the magnet 110 are formed.

In other words, the rotating shaft 109 is inserted into the rotating shaft insertion holes respectively provided in the lower board 103 and the upper board 104. Consequently, the filter moving member 105 can be rotated and displaced about the rotating shaft 109. A rotatable range of the filter moving member 105 is limited by the closed-time stopper 107 and the open-time stopper 108. A movable range of the magnet 110 is limited by the cutouts for guide respectively provided in the lower board 103 and the upper board 104.

With the configuration explained above, when the filter moving member 105 is rotated and displaced about the rotating shaft 109, for example, if the optical filter section 118 comes into contact with the closed-time stopper 107, a center of the optical filter 117a and a center of the optical opening 111 coincide with each other.

In the first arrangement state (the interposed state) of the filter switching device 39a, for example, as shown in FIG. 3, the shape memory alloy wire 120 contracts according to application of a voltage corresponding to the control by the processor 3. The magnet 119 fixed to one end of the shape memory alloy wire 120 is displaced to the tube 122 side against repulsion force of the bias spring 121. Therefore, an N pole of the magnet 110 and an N pole of the magnet 119 are arranged in positions opposed to each other.

Consequently, in the first arrangement state (the interposed state), repulsion is generated between the magnet 110 and the magnet 119 and the magnet 110 is displaced toward a center direction of the filter switching mechanism 101. As a result, in the first arrangement state (the interposed state), for example, as shown in FIG. 2, the filter moving member 105 rotates counterclockwise about the rotating shaft 109 and the optical filter section 118 comes into contact with the closed-time stopper 107.

In the first arrangement state (the interposed state), the optical opening 111 is covered with the optical filter section 118. Therefore, the filter switching mechanism 101 allows only return light in a predetermined wavelength band specified by the optical filter 117a to pass to the image pickup surface of the CCD 14.

On the other hand, with the configuration explained above, when the filter moving member 105 is rotated and displaced about the rotating shaft 109, for example, when the optical filter section 118 comes into contact with the open-time stopper 108, the optical filter section 118 is completely retracted from the optical opening 111.

In the second arrangement state (the retracted state) of the filter switching device 39a, for example, as shown in FIG. 5, the shape memory alloy wire 120 expands according to application of a voltage corresponding to the control by the processor 3. The magnet 119 fixed to one end of the shape memory alloy wire 120 is displaced to an opposite side of the tube 122 according to the repulsion force of the bias spring 121. Therefore, an S pole of the magnet 110 and the N pole of the magnet 119 are arranged in positions opposed to each other.

Consequently, in the second arrangement state (the retracted state), attraction is generated between the magnet 110 and the magnet 119 and the magnet 110 is displaced toward an outer peripheral direction of the filter switching mechanism 101. As a result, in the second arrangement state (the retracted state), for example, as shown in FIG. 4, the filter moving member 105 rotates clockwise about the rotating shaft 109 and the optical filter section 118 comes into contact with the open-time stopper 108.

In the second arrangement state (the retracted state), since the optical opening 111 is not covered with the optical filter section 118, the filter switching mechanism 101 does not perform band limitation for return light passed through the object optical system 14b and allows the return light to directly pass to the image pickup surface of the CCD 14.

Figure 6:
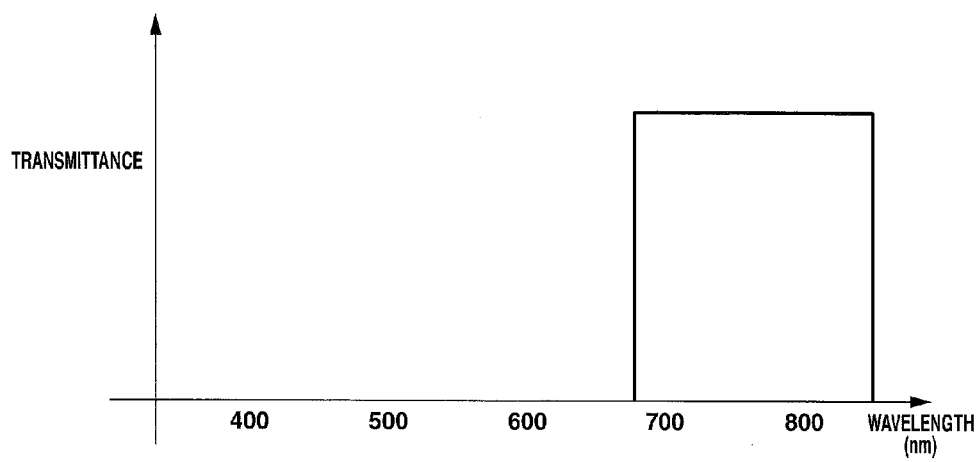
FIG. 6 is a graph showing a characteristic of the optical filter provided in the image pickup actuator.

FIG. 6 is a graph showing a characteristic of the optical filter provided in the image pickup actuator.

For example, as shown in FIG. 6, the optical filter 117a of the filter switching device 39a according to this embodiment is formed to allow only light in 680 to 850 nm to pass without generally attenuating the light.

The image pickup actuator 39 according to this embodiment includes, as shown in FIG. 1, the filter switching device 39a and a filter switching device 39b having a configuration substantially the same as a configuration of the filter switching device 39a.

Figure 7:
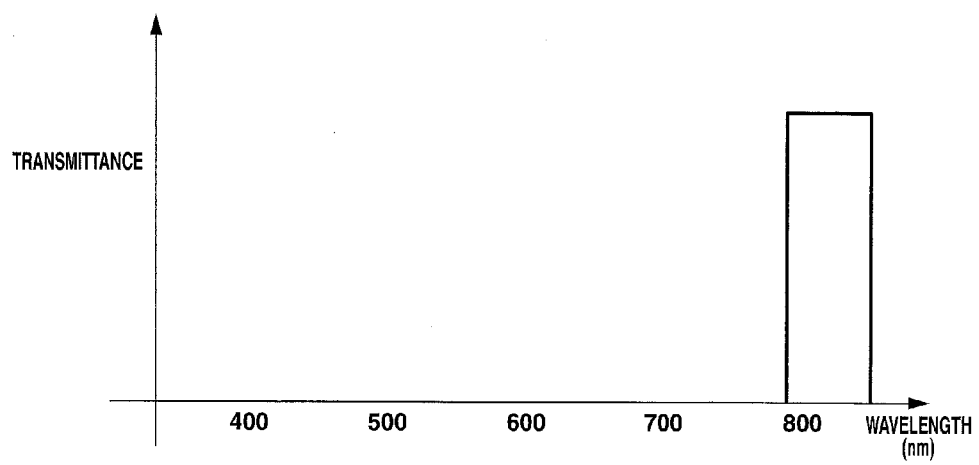
FIG. 7 is a graph showing a characteristic of an optical filter provided in the image pickup actuator and different from the optical filter shown in FIG. 6.

FIG. 7 is a graph showing a characteristic of an optical filter provided in the image pickup actuator and different from the optical filter shown in FIG. 6.

The filter switching device 39b includes an optical filter 117b that allows only return light in a wavelength band different from the wavelength band of the optical filter 117a to pass. Otherwise, the filter switching device 39b includes a configuration same as the configuration of the filter switching device 39a. For example, as shown in FIG. 7, the optical filter 117b is formed to allow only light in 790 to 850 nm to pass without generally attenuating the light.

The image pickup actuator 39 according to this embodiment is not limited to the image pickup actuator configured based on the configuration of the light adjusting device described in Japanese Patent Application Laid-Open Publication No. 2009-8717 explained above. Specifically, the image pickup actuator 39 according to this embodiment may be configured based on another configuration such as the light adjusting device described in Japanese Patent Application Laid-Open Publication No. 2009-8719 as long as the image pickup actuator 39 includes the configuration capable of switching the first arrangement state (the interposed state) and the second arrangement state (the retracted state) concerning each of the optical filters 117a and the 117b.

The light source device 1 includes a lamp 7 that emits light in a wavelength region including a visible region and a near infrared region, a switching filter 8 provided to vertically traverse an optical path of the lamp 7, a motor 9 that switches a filter interposed on the optical path of the lamp 7 to one of filters of the switching filter 8, a rotating filter 10 provided to vertically traverse the optical path of the lamp 7, a motor 11 that drives to rotate the rotating filter 10, an aperture 12 arranged on the optical path of the lamp 7 from the switching filter 8 to the rotating filter 10, and a condensing lens 12a that condenses illumination light passed through the rotating filter 10 on an end face on a light incident side of the light guide 13.

Figure 8:
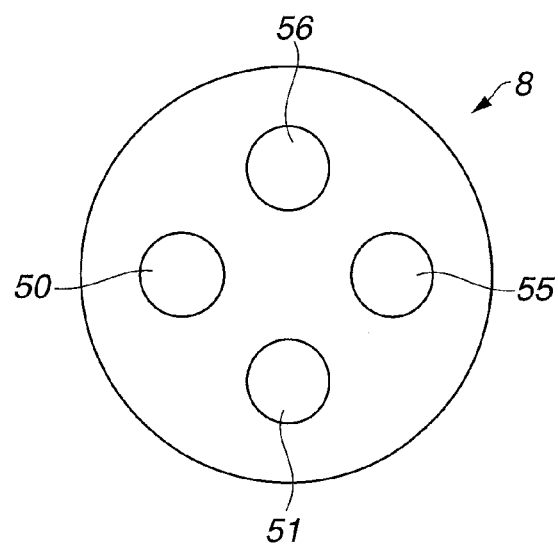
FIG. 8 is a diagram showing an example of a configuration of a switching filter provided in a light source device.

FIG. 8 is a diagram showing an example of a configuration of the switching filter provided in the light source device.

As shown in FIG. 8, in the switching filter 8 having a disk shape, a normal light filter 50 that allows light in the visible region to pass, a first excitation light filter 51 that allows light in a part of the visible region and in a red region to pass, a second excitation light filter 55 that allows light in a part of the visible region and in the near infrared region to pass, and a third excitation light filter 56 having both pass bands of the first excitation light filter 51 and the second excitation light filter 55 are provided along a peripheral direction of the disk. In other words, the motor 9 rotates according to the control by the processor 3, whereby, in the switching filter 8, any one of the normal light filter 50, the first excitation light filter 51, the second excitation light filter 55, and the third excitation light filter 56 is interposed on the optical path of the lamp 7 and the other three filters other than the one filter are retraced from the optical path of the lamp 7.

Figure 9:
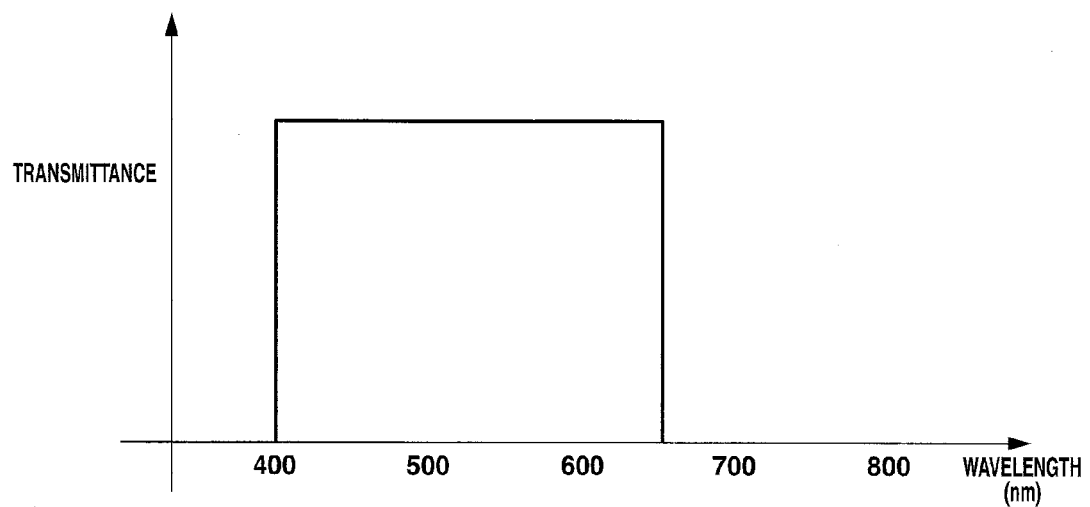
FIG. 9 is a graph showing a characteristic of a normal light filter provided in the switching filter.

FIG. 9 is a graph showing a characteristic of the normal light filter provided in the switching filter.

As shown in FIG. 9, the normal light filter 50 is formed to allow light in a wavelength band of 400 to 650 nm among lights in wavelength bands emitted from the lamp 7 to pass without generally attenuating the light.

Figure 10:
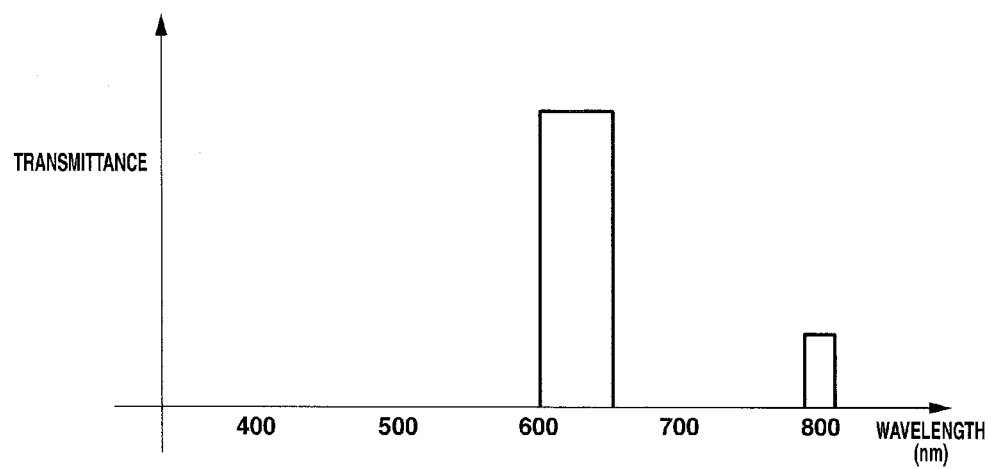
FIG. 10 is a graph showing a characteristic of a first excitation light filter provided in the switching filter.

FIG. 10 is a graph showing a characteristic of the first excitation light filter provided in the switching filter.

As shown in FIG. 10, the first excitation light filter 51 is formed to allow light in a wavelength band of 600 to 650 nm among lights in wavelength bands emitted from the lamp 7 to pass without generally attenuating the light and attenuate light in a wavelength band of 790 to 810 nm to predetermined intensity and allow the light to pass.

Figure 11:
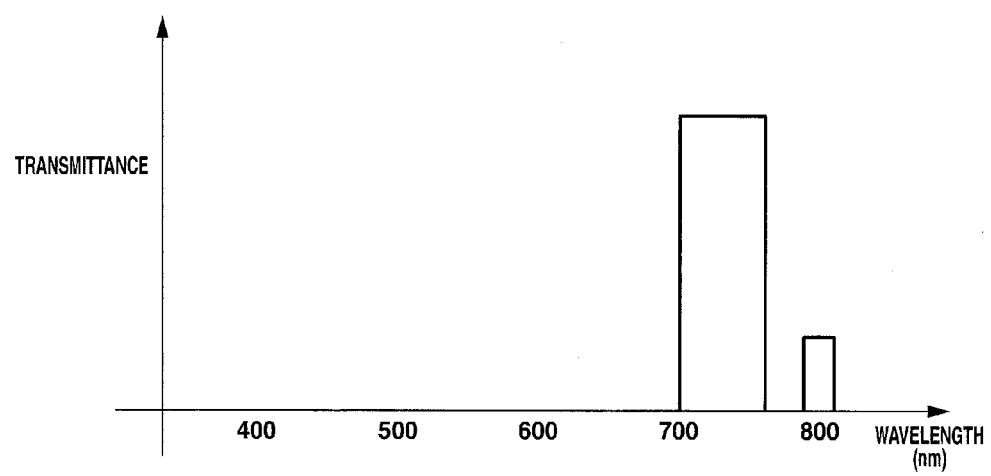
FIG. 11 is a graph showing a characteristic of a second excitation light filter provided in the switching filter.

FIG. 11 is a graph showing a characteristic of the second excitation light filter provided in the switching filter.

As shown in FIG. 11, the second excitation light filter 55 is formed to allow light in a wavelength band of 700 to 760 nm among the lights in the wavelength bands emitted from the lamp 7 to pass without generally attenuating the light and attenuate the light in the wavelength band of 790 to 810 nm to predetermined intensity and allow the light to pass.

Figure 12:
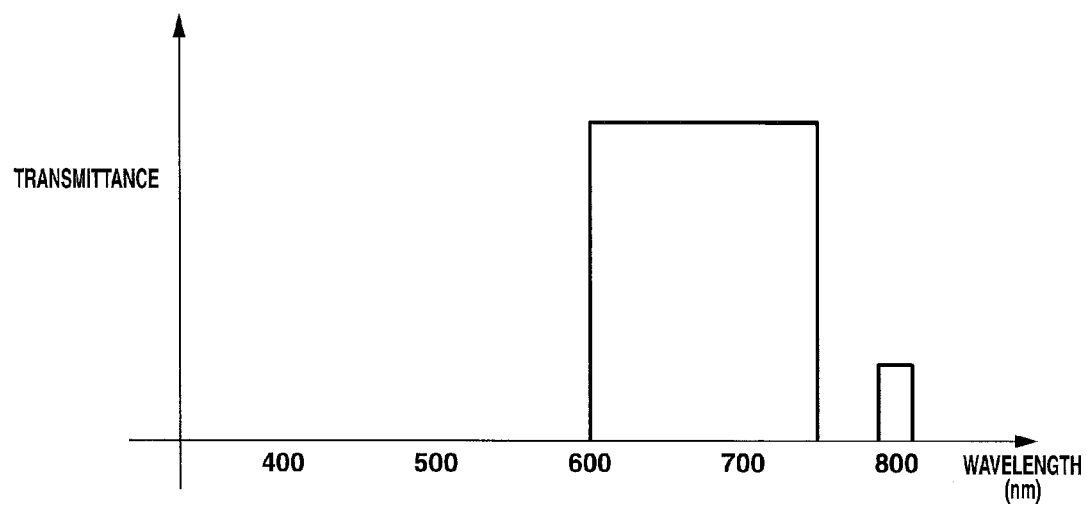
FIG. 12 is a diagram showing a characteristic of a third excitation light filter provided in the switching filter.

FIG. 12 is a diagram showing a characteristic of the third excitation light filter provided in the switching filter.

As shown in FIG. 12, the third excitation light filter 56 is formed to allow light in a wavelength band of 600 to 760 nm among the lights in the wavelength bands emitted from the lamp 7 to pass without generally attenuating the light and attenuate the light in the wavelength band of 790 to 810 nm to predetermined intensity and allow the light to pass.

The aperture 12 includes a configuration capable of increasing and reducing, according to the control by the processor 3, an intensity of light passed through the switching filter 8.

Figure 13:
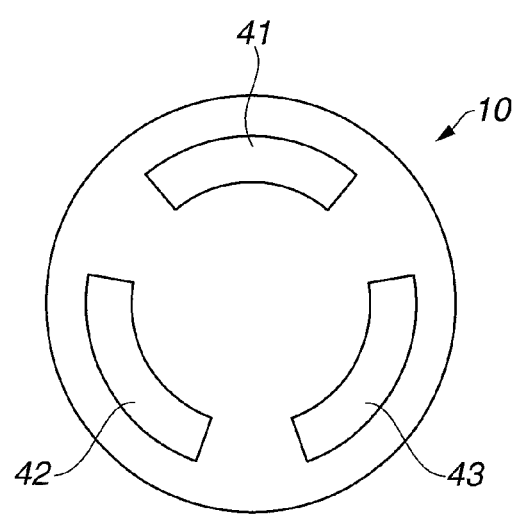
FIG. 13 is a diagram of an example of a configuration of a rotating filter provided in the light source device.

FIG. 13 is a diagram showing an example of a configuration of the rotating filter provided in the light source device.

As shown in FIG. 13, in the rotating filter 10 having a disk shape, an optical filter 41 that allows light in a red region to pass, an optical filter 42 that allows light in a green region to pass, and an optical filter 43 that allows light in a blue region and a near infrared region to pass are provided along a circumferential direction of a disk. Specifically, the rotating filter 10 is configured such that the motor 11 rotates according to the control by the processor 3 (a timing signal of a timing generator 30 explained later), whereby the rotating filter 10 is interposed on the optical path of the lamp 7 or retracted from the optical path of the lamp 7 while the optical filters 41, 42, and 43 are sequentially interchanged. The rotating filter 10 according to this embodiment is formed not to allow light to pass when places other than the places where the optical filters 41, 42, and 43 are arranged are interposed on the optical path of the lamp 7.

Figure 14:
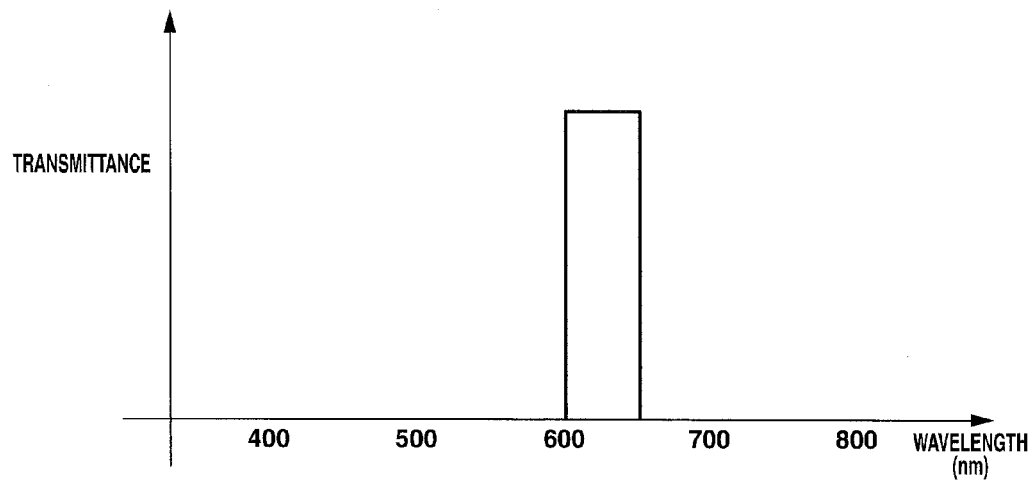
FIG. 14 is a graph showing a characteristic of an optical filter provided in the rotating filter.

FIG. 14 is a graph showing a characteristic of the optical filter provided in the rotating filter.

As shown in FIG. 14, the optical filter 41 is formed to allow the light in the wavelength band of 600 to 650 nm among the wavelength bands of the light passed through the switching filter 8 and the aperture 12 to pass without generally attenuating the light.

Figure 15:
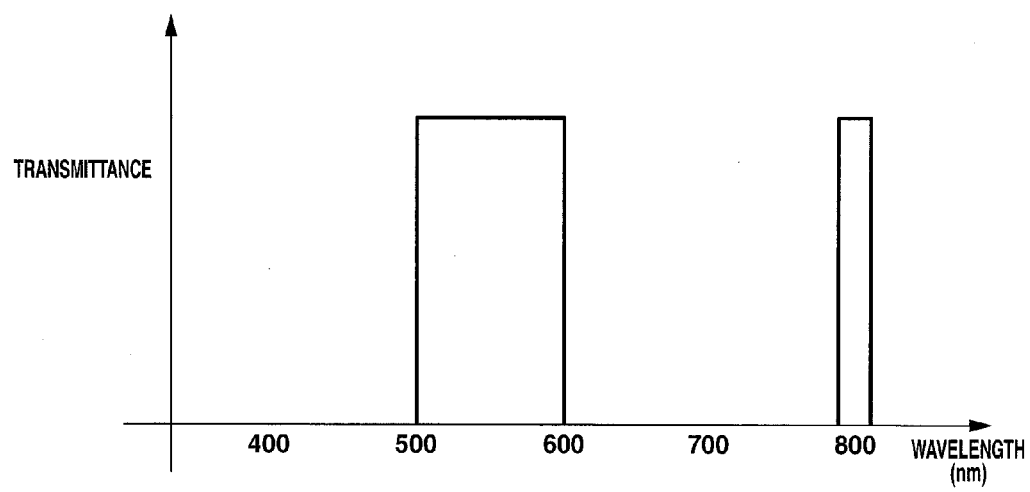
FIG. 15 is a graph showing a characteristic of an optical filter provided in the rotating filter and different from the optical filter shown in FIG. 14.

FIG. 15 is a graph showing a characteristic of an optical filter provided in the rotating filter and different from the optical filter shown in FIG. 14.

As shown in FIG. 15, the optical filter 42 is formed to allow light in a wavelength band of 500 to 600 nm and the light in the wavelength band of 790 to 810 nm among the wavelength bands of the light passed through the switching filter 8 and the aperture 12 to pass without generally attenuating the light.

Figure 16:
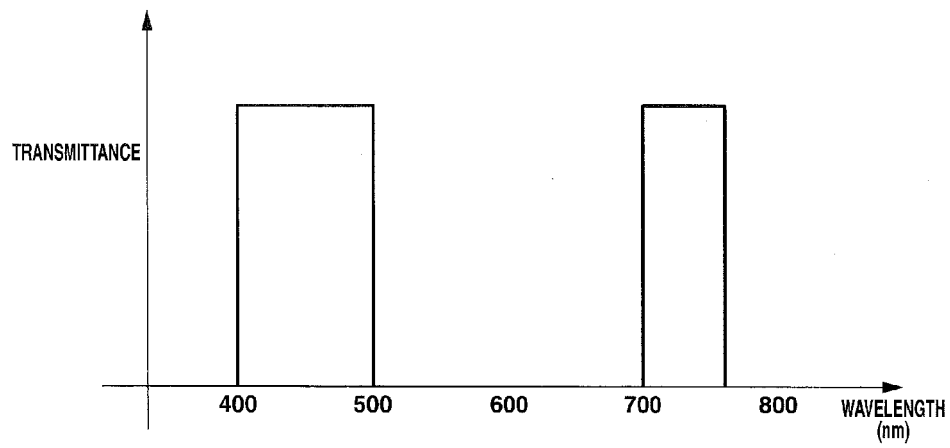
FIG. 16 is a graph showing a characteristic of an optical filter provided in the rotating filter and different from the optical filters shown in FIGS. 14 and 15.

FIG. 16 is a graph showing a characteristic of an optical filter provided in the rotating filter and different from the optical filters shown in FIGS. 14 and 15.

As shown in FIG. 16, the optical filter 43 is formed to allow lights in wavelength bands of 400 to 500 nm and 700 to 760 nm among the wavelength bands of the light passed through the switching filter 8 and the aperture 12 to pass.

An image pickup signal outputted from the CCD 14 is, after being inputted to the processor 3, subjected to processing such as CDS (correlated double sampling) in a pre-process circuit 18 and, after being converted into a digital image signal in an A/D conversion circuit 19, outputted to a color balance correcting circuit 20.

The color balance correcting circuit 20 selects, based on a timing signal from the timing generator 30, color balance correction coefficients respectively corresponding to the optical filters 41, 42, and 43 of the rotating filter 10 to be synchronized with timing when the optical filters 41, 42, and 43 are sequentially interposed on the optical path of the lamp 7 and reads the selected color balance correction coefficient from a not-shown memory. After multiplying the color balance correction coefficients read from the not-shown memory with image signals sequentially outputted from the A/D conversion circuit 19, the color balance correcting circuit 20 outputs the image signals after the multiplication to a multiplexer 21.

The color balance correction coefficients are correction values calculated by processing of a control section 33 (a processing circuit 33a) in a color balance operation of white balance or the like. As a processing result of the processing, the color balance correction coefficients are stored in the not-shown memory of the color balance correcting circuit 20.

The color balance operation of white balance or the like is started at timing when the control section 33 detects that operation related to start of execution of the color balance operation is performed in a color balance setting switch (not shown) provided in an input switch group 60 of the processor 3.

The multiplexer 21 outputs, based on the timing signal from the timing generator 30, the image signals outputted from the color balance correcting circuit 20 while apportioning the image signals to synchronization memories 22a, 22b, and 22c as appropriate to be synchronized with the timing when the optical filters 41, 42, and 43 are sequentially interposed on the optical path of the lamp 7.

The synchronization memories 22a, 22b, and 22c include a configuration capable of temporarily storing the image signals outputted from the multiplexer 21.

After simultaneously reading the image signals stored in the synchronization memories 22a, 22b, and 22c, the image processing circuit 23 applies predetermined image processing to the read three image signals. The image processing circuit 23 allocates the three image signals after the predetermined image processing respectively to a first color channel equivalent to a first color component (e.g., a red (R) component), a second color channel equivalent to a second color component (e.g., a green (G) component), and a third color channel equivalent to a third color component (e.g., a blue (B) component) and outputs the image signals to a tone adjusting circuit 24.

After reading a tone adjustment coefficient stored in a not-shown memory, the tone adjusting circuit 24 performs matrix processing using the tone adjustment coefficient and the image signal of the first color component (the first color channel), the image signal of the second color component (the second color channel), and the image signal of the third color component (the third color channel) outputted from the image processing circuit 23. Thereafter, the tone adjusting circuit 24 applies gamma correction processing to the image signal of the first color component, the image signal of the second color component, and the image signal of the third color component subjected to the matrix processing. The tone adjusting circuit 24 outputs the image signals of the first color component, the second color component, and the third color component subjected to the gamma correction processing to an encoding circuit 26 and a light adjusting circuit 27. The tone adjusting circuit 24 outputs the image signal of the first color component subjected to the gamma correction processing to a D/A conversion circuit 25a, outputs the image signal of the second color component subjected to the gamma correction to a D/A conversion circuit 25b, and outputs the image signal of the third color component subjected to the gamma correction processing to a D/A conversion circuit 25c.

The tone adjustment coefficient is an adjustment value calculated from processing of the control section 33 (the processing circuit 33a) in a tone adjusting operation. As a processing result of the processing, the tone adjustment coefficient is stored in the not-shown memory of the tone adjusting circuit 24. The tone adjusting operation is started at timing when the control section 33 detects that operation related to a change of a tone displayed on the monitor 4 is performed in a tone setting switch (not shown) provided in the input switch group 60. When the operation related to the change of the tone displayed on the monitor 4 is performed, the control section 33 (the processing circuit 33a) performs processing for calculating a tone adjustment coefficient corresponding to the tone after the change.

The image signals of the first color component, the second color component, and the third color component outputted from the tone adjusting circuit 24 are outputted to the monitor 4 after being respectively converted into analog video signals in the D/A conversion circuits 25a, 25b, and 25c. Consequently, the monitor 4 displays observation images corresponding to respective observation modes.

The image signals of the first color component, the second color component, and the third color component outputted from the tone adjusting circuit 24 are outputted to the digital filing device 5 and the photographing device 6 after being subjected to encoding processing in the encoding circuit 26. Consequently, the digital filing device 5 records and stores a still image at the time when the control section 33 detects input operation in the release switch 16. The photographing device 6 photographs a still image at the time when the control section 33 detects input operation in the release switch 16.

The light adjusting circuit 27 performs, based on respective signal levels of the image signals of the first color component, the second color component, and the third color component outputted from the tone adjusting circuit 24, control for the aperture 12 such that illumination light having an appropriate intensity corresponding to an observation mode is supplied from the light source device 1. The light adjusting circuit 27 performs control for changing an amplification ratio of an amplification ratio control circuit 29.

An exposure time control circuit 28 controls, based on a timing signal outputted from the timing generator 30 and an output signal from the control section 33, an electronic shutter of the CCD 14 to be synchronized with the timing when the optical filters 41, 42, and 43 are sequentially interposed on the optical path of the lamp 7 and to correspond to the output signal from the control section 33. Exposure time in the CCD 14 is changed according to such control for the electronic shutter.

The amplification ratio control circuit 29 controls, based on control by the light adjusting circuit 27 and a timing signal outputted from the timing generator 30, a charge amplifying device of the CCD 14 to be synchronized with the timing when the optical filters 41, 42, and 43 are sequentially interposed on the optical path of the lamp 7 and to have an amplification ratio corresponding to the control by the light adjusting circuit 27. An amplification ratio in the CCD 14 is changed according to such control for the charge amplifying device.

The timing generator 30 generates and outputs a timing signal for appropriately synchronizing operations of the respective sections of the endoscope system 301.

A CCD driver 31 drives, based on a timing signal outputted from the timing generator 30, the CCD 14 to be synchronized with the timing when the optical filters 41, 42, and 43 are sequentially interposed on the optical path of the lamp 7.

An image pickup actuator control circuit 32 applies, to the image pickup actuator 39, based on a timing signal outputted from the timing generator 30, control for synchronizing the timing when the optical filters 41, 42, and 43 are sequentially interposed on the optical path of the lamp 7, switching timing of an arrangement state of the optical filter 117a in the filter switching device 39a, and switching timing of an arrangement state of the optical filter 117b in the filter switching device 39b.

The control section 33 including a CPU and a memory includes the processing circuit 33a that performs processing, a storing circuit 33b, a timing circuit 33c, a determining circuit 33d, and a switching control circuit 33e.

In the storing circuit 33b, various data used for, for example, the processing of the processing circuit 33a such as table data explained below are stored.

The timing circuit 33c includes an RTC (real time clock), a timer and the like, and is configured to be capable of measuring, for each fluorescent drug, elapsed time after a fluorescent drug is administered to a subject.

The determining circuit 33d performs, at any time, determination processing explained below based on a processing result of the processing circuit 33a and a measurement result of the timing circuit 33c.

The switching control circuit 33e applies, for example, to the motor 9 of the light source device 1, control based on a detection result of an operation state in the mode switching switch 15 of the scope 2 connected to the processor 3 and a determination result of the determining circuit 33d.

On the other hand, the input switch group 60 of the processor 3 is provided with plural switches such as a tone setting switch with which operation concerning a change of a tone of an image displayed on the monitor 4 can be performed, a color balance setting switch with which operation concerning a color balance operation of white balance or the like can be performed, and an image display selection switch with which operation concerning switching of a display form of an observation image displayed on the monitor 4 can be performed. The control section 33 detects operation states of the switches provided in the input switch group 60 of the processor 3 and performs control, processing, and the like corresponding to a detection result.

The control section 33 detects an operation state in the release switch 16 of the scope 2 connected to the processor 3 and performs, according to a detection result, control related to recording of a still image in the digital filing device 5 and (or) photographing of a still image in the photographing device 6.

When the scope 2 is connected to the processor 3, the control section 33 reads information stored in the scope discriminating device 17 and performs control corresponding the read information.

The control section 33 according to this embodiment is connected to the respective sections of the processor 3 via a not-shown signal line or the like to be capable of applying comprehensive control to the respective sections of the processor 3.

A notification signal generating circuit 61 generates a character signal for displaying a predetermined character string capable of notifying information concerning a determination result of the determining circuit 33d of the control section 33 and outputs the character signal to the monitor 4. The notification signal generating circuit 61 generates a sound signal for generating predetermined sound capable of notifying information concerning a determination result of the determining circuit 33d of the control section 33 and outputs the sound signal to the speaker 63. The notification signal generating circuit 61 according to this embodiment only has to be configured to be capable of outputting at least one of the character signal and the sound signal.

Action of the endoscope system 301 according to this embodiment is explained below.

First, a surgeon or the like connects the respective sections of the endoscope system 301 and turns on a power supply to thereby start operations of the respective sections.

According to the turn-on of the power supply for the processor 3, output of a timing signal from the timing generator 30 is started.

Figure 17:
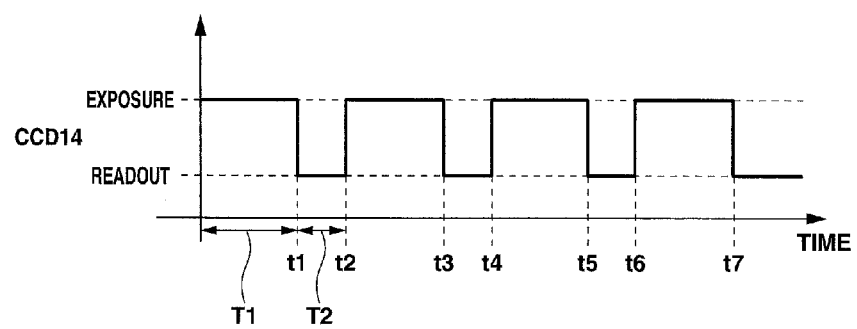
FIG. 17 is a timing chart showing an exposure period and a readout period of a CCD provided in a scope.

FIG. 17 is a timing chart showing an exposure period and a readout period of the CCD provided in the scope.

The CCD driver 31 drives, based on a timing signal from the timing generator 30, the CCD 14 according to, for example, the timing chart shown in FIG. 17. Consequently, the CCD 14 operates such that an exposure period T1 serving as a period related to accumulation of charges and a readout period T2 serving as a period related to flushing of the charges accumulated in the exposure period T1 are alternately interchanged.

Figure 18:
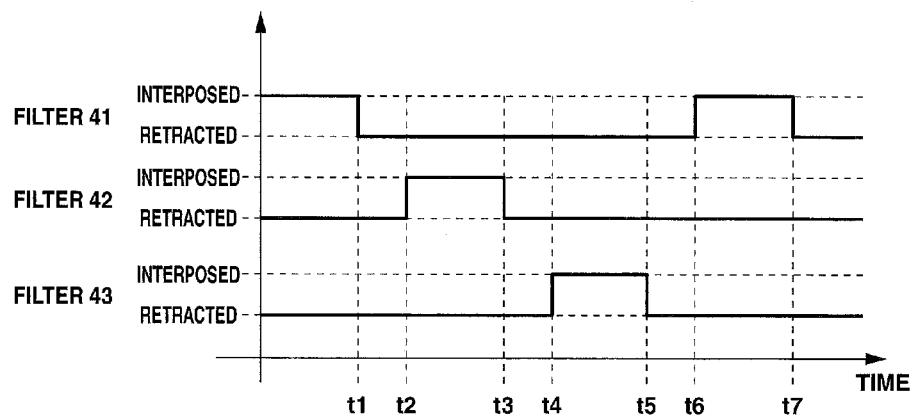
FIG. 18 is a timing chart showing an interposing action and a retracting action of the optical filters involved in rotation of the rotating filter.

FIG. 18 is a timing chart showing an interposing action and a retracting action of the respective optical filters involved in the rotation of the rotating filter.

According to the turn-on of the power supply for the light source device 1 and start of output of the timing signal from the timing generator 30, rotation driving of the motor 11 is started. According to the rotation driving of the motor 11, the optical filters 41, 42, and 43 are interposed on the optical path of the lamp 7 and retracted from the optical path of the lamp 7 while being sequentially interchanged. The interposing action and the retracting action of the optical filters 41, 42, and 43 involved in the rotation driving of the motor 11 are performed according to, for example, timing corresponding to the timing chart shown in FIG. 18. Specifically, the motor 11 rotates the rotating filter 10 to sequentially interpose the optical filters 41, 42, and 43 on the optical path of the lamp 7 in the exposure period of the CCD 14 and retract the optical filters 41, 42, and 43 from the optical path of the lamp 7 in the readout period of the CCD 14.

On the other hand, after connecting the respective sections of the endoscope system 301 and turning on the power supply, the surgeon or the like operates the keyboard 62 to thereby (cause the monitor 4 to display, for example, a setting screen related to various kinds of setting of the processor 3 and) sets a reference value Ns of an accumulation amount at diagnosis start and a reference value Ne of an accumulation amount at diagnosis end in observation performed by using a fluorescent drug. The surgeon or the like administers the fluorescent drug to the observation target region 201 of the subject at a point either before or after the setting of the reference values Ns and Ne.

The reference values Ns and Ne are values indicating ratios set when a maximum value Nmax equivalent to a peak value of the accumulation amount of the fluorescent drug is set to 10%. In an initial state, the reference values Ns and Ne are stored in the storing circuit 33b in a state in which the values are set as Ns=Ne=Nmax.

Depending on a combination of a type of a fluorescent drug in use and an organ to which a target region to which the fluorescent drug is administered (the observation garget region 201) belongs and a method of administering the fluorescent drug to the target region, sufficient diagnosability can be obtained even if the reference values Ns and Ne are respectively values other than Nmax. Therefore, the reference values Ns and Ne may be able to be respectively set to arbitrary values according to operation of the keyboard 62 or may be able to be selected one by one out of predetermined plural values (such as 80%, 60%, and the like).

When the control section 33 detects that new reference values Ns and Ne are set according to the operation of the keyboard 62, the control section 33 updates the reference values Ns and Ne stored in the storing circuit 33b.

After performing the setting of the reference values Ns and Ne, the surgeon or the like further operates the keyboard 62 to thereby input, for each kind of fluorescence in a wavelength band observable by the endoscope system 301, one set of kinds of information such as a type of a fluorescent drug in use, an organ to which a target region to which the fluorescent drug is administered (the observation target region 201) belongs, a method of administering the fluorescent drug to the target region, and start time of administration of the fluorescent drug to the subject. Specifically, with the endoscope system 301 according to this embodiment, fluorescence in a first wavelength band (680 to 750 nm) excited by radiation of light in the wavelength band of 600 to 650 nm and fluorescence in a second wavelength band (790 to 850 nm) excited by radiation of light in the wavelength band of 700 to 760 nm can be observed. Therefore, two sets of the information are inputted.

On the other hand, the processing circuit 33a of the control section 33 selects one table data coinciding with a type of the fluorescent drug in use out of table data stored in the storing circuit 33b in advance.

FIG. 19 is a diagram showing an example of table data used in selecting a drug kinetics of the fluorescent drug.

The table data is stored in the storing circuit 33b in advance in a state in which information concerning a drug kinetics in a living body is classified for each of plural kinds of fluorescent drugs.

When the fluorescent drug in use is a fluorescent drug A, the processing circuit 33a of the control section 33 selects the table data illustrated in FIG. 19.

Further, the processing circuit 33a of the control section 33 selects, out of the selected one table data, one drug kinetics corresponding to a combination of an organ to which a target region to which the fluorescent drug is administered (the observation target region 201) belongs and a method of administering the fluorescent drug to the target region.

Specifically, when the target region to which the fluorescent drug is administered (the observation target region 201) belongs to a stomach and the fluorescent drug is administered by an intravenous injection, the processing circuit 33a of the control section 33 selects, for example, a drug kinetics A02 in the table data shown in FIG. 19.

According to this embodiment, for example, the reference values Ns and Ne are set in advance for each of drug kinetics in the table data stored in the storing circuit 33b, whereby the reference values Ns and Ne may be uniquely decided according to selection of one drug kinetics.

The processing circuit 33a of the control section 33 matches, based on the reference values Ns and Ne stored in the storing circuit 33b and the start time of administration of the fluorescent drug to the subject, a point of elapsed time T=0 from the administration of the fluorescent drug to the subject and an accumulation amount N=0 of the fluorescent drug to the start time of the administration in the one drug kinetics selected by the processing, acquires diagnosis start time Ts equivalent to first elapsed time T when the accumulation amount N=Ns, and further acquires diagnosis end time Te equivalent to last elapsed time T when the accumulation amount N=Ne last after the diagnosis start time Ts.

FIG. 20 is a graph showing an example of a drug kinetics selected out of the table data. FIG. 21 is a diagram showing an example of diagnosis start time and diagnosis end time acquired when the drug kinetics shown in FIG. 20 is selected.

The drug kinetics of the fluorescent drug in the living body has, for example, a correlation shown in FIG. 20 between the elapsed time T from administration of the fluorescent drug into a body of the subject to discharge and the accumulation amount N in the target region in the body of the subject to which the fluorescent drug is administered (the observation target region 201). Therefore, for example, when the drug kinetics shown in FIG. 20 is selected as the drug kinetics of the fluorescent drug and both the reference values Ns and Ne are set as Nmax, the diagnosis start time Ts and the diagnosis end time Te shown in FIG. 21 are acquired.

When the fluorescent drug is directly sprayed and administered to the target region, unlike the administration by the intravenous injection or the like, time immediately after the fluorescent drug is actually sprayed to the target region is equivalent to start time of the administration to the subject, i.e., time when the elapsed time T=0 and the accumulation amount N=0 of the fluorescent drug. In view of such points, when the fluorescent drug is directly sprayed and administered to the target region, the time equivalent to the elapsed time T=0 and the accumulation amount N=0 of the fluorescent drug is set to, for example, time when an administration start time notification switch (not shown) provided in the input switch group 60 is pressed rather than an administration start time inputted according to operation of the keyboard 62. Consequently, it is possible to acquire accurate diagnosis start time Ts and diagnosis end time Te.

The administration start time notification switch is not limited to the switch provided in the input switch group 60 of the processor 3 and may be a switch provided in, for example, the scope 2. Therefore, for the purpose of preventing an operation mistake, for example, when the administration start time notification switch provided in the scope 2 is pressed long, time equivalent to the elapsed time T=0 and the accumulation amount N=0 of the fluorescent drug may be acquired. Further, after the time equivalent to the elapsed time T=0 and the accumulation amount N=0 of the fluorescent drug is acquired, another function may be allocated to the administration start time notification switch provided in the scope 2. Specifically, after the time equivalent to the elapsed time T=0 and the accumulation amount N=0 of the fluorescent drug is acquired, for example, a function equivalent to any one switch selected in advance by the surgeon or the like among the plural switches (the tone setting switch, the color balance setting switch, the image display selection switch, etc.) provided in the input switch group 60 of the processor 3 may be allocated to the administration start time notification switch of the scope 2.

On the other hand, the determining circuit 33d of the control section 33 performs, at any time, based on the diagnosis start time Ts and the diagnosis end time Te acquired by the processing circuit 33a and a measurement result of the timing circuit 33c, determination concerning whether present time is equivalent to time within diagnosable time, which is a time period from the diagnosis start time Ts to the diagnosis end time Te. In other words, the determining circuit 33d of the control section 33 is configured to be capable of performing, based on the diagnosis start time Ts and the diagnosis end time Te acquired by the processing circuit 33a and a measurement result of the timing circuit 33c, determination concerning whether the present time reaches the diagnosis start time Ts and determination concerning whether the present time reaches the diagnosis end time Te.

If a determination result that the present time is not within the diagnosable time is obtained by the determining circuit 33d, the notification signal generating circuit 61 generates a character signal for displaying a character string for notifying that the present time is in a time period when switching to an observation mode for radiating excitation light corresponding to the administered fluorescent drug is impossible and outputs the character signal to the monitor 4. If the determination result that the present time is not within the diagnosable time is obtained from the determining circuit 33d, the notification signal generating circuit 61 generates a sound signal for generating sound for notifying that the present time is in a time period when switching to an observation mode for radiating excitation light corresponding to the administered fluorescent drug is impossible and outputs the sound signal to the speaker 63.

If a determination result that the present time is not within the diagnosable time is obtained by the determining circuit 33d, even if switching operation to the observation mode for radiating the excitation light corresponding to the administered fluorescent drug is performed in the mode switching switch 15, the switching control circuit 33e of the control section 33 operates to disable the switching operation. If a determination result that the present time is within the diagnosable time is obtained by the determining circuit 33d, when the switching operation to the observation mode for radiating the excitation light corresponding to the administered fluorescent drug is performed in the mode switching switch 15, the switching control circuit 33e of the control section 33 applies control corresponding to the switching operation to, for example, the motor 9 of the light source device 1. If a determination result that the present time does not reach the diagnosis end time Te, i.e., 0≤T≤Te is obtained by the determining circuit 33d, the switching control circuit 33e of the control section 33 applies predetermined control to the light adjusting circuit 27 or the like when the observation mode is switched to a fourth observation mode explained below.

In an example explained below, in the endoscope system 301 according to this embodiment, for example, concerning an operation performed in switching of an observation mode, a first fluorescent drug that is excited by radiation of light in the wavelength band of 600 to 650 nm and emits fluorescence in the first wavelength band (680 to 750 nm) and a second fluorescent drug that is excited by radiation of light in the wavelength band of 700 to 760 nm and emits fluorescence in the second wavelength band (790 to 850 nm) are administered to the same subject and observation of the observation target region 201 is performed.

If a determination result that the present time is within diagnosable time of the first fluorescent drug is obtained by the determining circuit 33d, when switching operation to a first observation mode for radiating excitation light corresponding to the first fluorescent drug is performed in the mode switching switch 15 (or when switching from another observation mode to the first observation mode is performed irrespective of an operation state of the mode switching switch 15), the switching control circuit 33e of the control section 33 interposes the first excitation light filter 51 on the optical path of the lamp 7 by controlling the motor 9 of the light source device 1. Specifically, in the first observation mode, frame-sequential first illumination light including reference light in the wavelength band of 790 to 810 nm and first excitation light in the wavelength band of 600 to 650 nm is supplied to the light guide 13.

Further, if a determination result that the present time is within the diagnosable time of the first fluorescent drug is obtained by the determining circuit 33d, when the switching operation to the first observation mode is performed in the mode switching switch 15 (or when the switching from another observation mode to the first observation mode is performed irrespective of an operation state of the mode switching switch 15), the switching control circuit 33e of the control section 33 controls the image pickup actuator control circuit 32 to thereby cause the image pickup actuator 39 to operate to synchronize the timing when the optical filters 41, 42, and 43 are sequentially interposed on the optical path of the lamp 7 and the switching timing of the arrangement state of the optical filter 117a in the filter switching device 39a.

Figure 22:
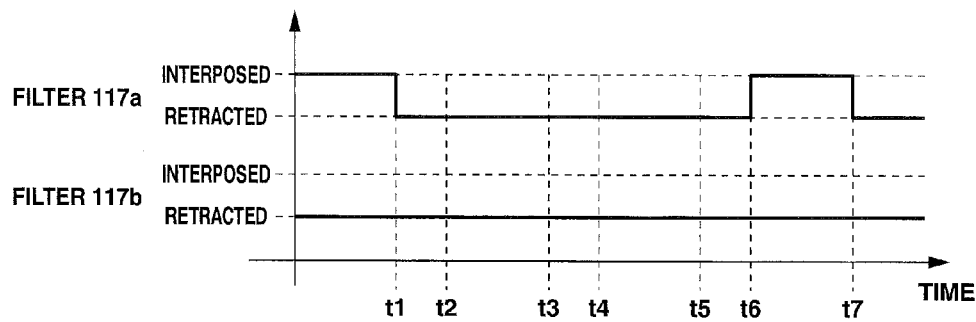
FIG. 22 is a timing chart showing interposing actions and retracting actions in a first observation mode of the respective optical filters provided in the image pickup actuator.

Specifically, as shown in FIGS. 17, 18, and 22, in the first observation mode, in the exposure period of the CCD 14 and the period in which the optical filter 41 is interposed on the optical path of the lamp 7, the image pickup actuator control circuit 32 sets the arrangement state of the optical filter 117a of the filter switching device 39a to a first arrangement state (an interposed state) and further sets the arrangement state of the optical filter 117b of the filter switching device 39b to a second arrangement state (a retracted state). On the other hand, as shown in FIGS. 17, 18, and 22, in the first observation mode, in the readout period of the CCD 14 and the period in which the optical filter 42 is interposed on the optical path of the lamp 7 or the period in which the optical filter 43 is interposed on the optical path of the lamp 7, the image pickup actuator control circuit 32 sets the arrangement state of the optical filter 117a of the filter switching device 39a to the second arrangement state (the retracted state) and further sets the arrangement state of the optical filter 117b of the filter switching device 39b to the second arrangement state (the retracted state).

Therefore, in the first observation mode, the first fluorescent drug is excited by first illumination light (first excitation light) emitted from the light guide 13. Therefore, the first fluorescence in the wavelength band of 680 to 750 nm and the reference light in the wavelength band of 790 to 810 nm are sequentially focused on the image pickup surface of the CCD 14 as return light from the observation target region 201.

If the determination result that the present time is not within the diagnosable time of the first fluorescent drug is obtained by the determining circuit 33d, even if the switching operation from another observation mode to the first observation mode is performed in the mode switching switch 15, the switching control circuit 33e of the control section 33 disables the switching operation by maintaining a control state of the motor 9 and the image pickup actuator control circuit 32 in a state before the switching operation is performed.

At a point if the determination result that the present time is within the diagnosable time of the first fluorescent drug is obtained by the determining circuit 33d, i.e., at a point when the present time reaches the diagnosis start time Ts of the first fluorescent drug, the switching control circuit 33e of the control section 33 may apply control for shifting the observation mode to the first observation mode to the motor 9 and the image pickup actuator control circuit 32 irrespective of an operation state of the mode switching switch 15.

If the determination result that the present time is not within the diagnosable time of the first fluorescent drug and the diagnosis end time Te of the first fluorescent drug elapses is obtained by the determining circuit 33d, the switching control circuit 33e of the control section 33 may disable the switching operation from another observation mode to the first observation mode and apply the control for switching the first observation mode to another observation mode (e.g., a fourth observation mode explained below) to the motor 9 and the image pickup actuator control circuit 32 irrespective of an operation state of the mode switching switch 15.

On the other hand, if the determination result that the present time is not within the diagnosable time of the first fluorescent drug is obtained by the determining circuit 33d, the notification signal generating circuit 61 generates a character signal for displaying a character string for informing that the present time is a time period when the switching to the first observation mode is impossible. The character signal includes a message that, for example, the present time does not reach the diagnosis start time Ts of the first fluorescent drug or the present time is after the diagnosis end time Te of the first fluorescent drug. The notification signal generating circuit 61 outputs the character signal to the monitor 4. Further, if the determination result that the present time is not within the diagnosable time of the first fluorescent drug is obtained by the determining circuit 33d, the notification signal generating circuit 61 generates a sound signal for generating sound for informing that the present time is a time period when the switching to the first observation mode is impossible. The sound signal includes a message that, for example, the present time does not reach the diagnosis start time Ts of the first fluorescent drug or the present time is after the diagnosis end time Te of the first fluorescent drug. The notification signal generating circuit 61 outputs the sound signal to the speaker 63.

The notification signal generating circuit 61 may operate, based on a determination result of the determining circuit 33d, to perform notification at points when the present time reaches the diagnosis start time Ts and the diagnosis end time Te of the first fluorescent drug or may operate to cause the monitor 4 to always display the diagnosis start time Ts and the diagnosis end time Te of the first fluorescent drug.

If a determination result that the present time is within diagnosable time of the second fluorescent drug is obtained by the determining circuit 33d, when switching operation to a second observation mode for radiating excitation light corresponding to the second fluorescent drug is performed in the mode switching switch 15 (or when switching from another observation mode to the second observation mode is performed irrespective of an operation state of the mode switching switch 15), the switching control circuit 33e of the control section 33 interposes the second excitation light filter 55 on the optical path of the lamp 7 by controlling the motor 9 of the light source device 1. Specifically, in the second observation mode, frame-sequential second illumination light including reference light in the wavelength band of 790 to 810 nm and second excitation light in the wavelength band of 700 to 760 nm is supplied to the light guide 13.

Further, if the determination result that the present time is within the diagnosable time of the second fluorescent drug is obtained by the determining circuit 33d, when the switching operation to the second observation mode is performed in the mode switching switch 15 (or when switching from another observation mode to the second observation mode is performed irrespective of an operation state of the mode switching switch 15), the switching control circuit 33e of the control section 33 controls the image pickup actuator control circuit 32 to thereby cause the image pickup actuator 39 to operate to synchronize the timing when the optical filters 41, 42, and 43 are sequentially interposed on the optical path of the lamp 7 and the switching timing of the arrangement state of the optical filter 117b in the filter switching device 39b.

Figure 23:
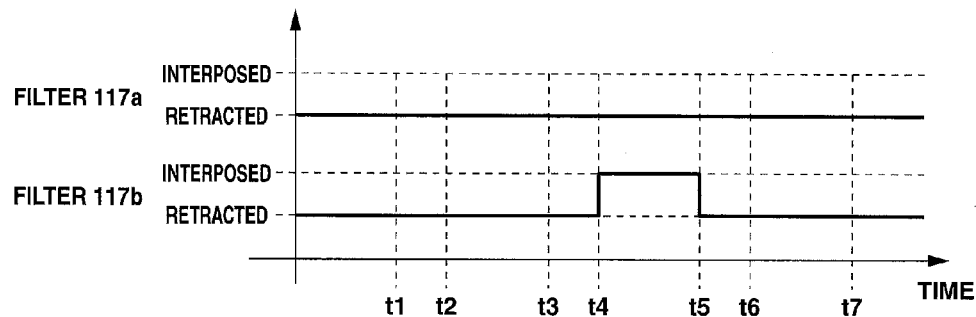
FIG. 23 is a timing chart showing interposing actions and retracting actions in a second observation mode of the respective optical filters provided in the image pickup actuators.

Specifically, as shown in FIGS. 17, 18, and 23, in the second observation mode, in the exposure period of the CCD 14 and the period in which the optical filter 43 is interposed on the optical path of the lamp 7, the image pickup actuator control circuit 32 sets the arrangement state of the optical filter 117a of the filter switching device 39a to the second arrangement state (the retracted state) and further sets the arrangement state of the optical filter 117b of the filter switching device 39b to the first arrangement state (the interposed state). On the other hand, as shown in FIGS. 17, 18, and 23, in the second observation mode, in the readout period of the CCD 14 and the period in which the optical filter 41 is interposed on the optical path of the lamp 7 or the period in which the optical filter 42 is interposed on the optical path of the lamp 7, the image pickup actuator control circuit 32 sets the arrangement state of the optical filter 117a of the filter switching device 39a to the second arrangement state (the retracted state) and further sets the arrangement state of the optical filter 117b of the filter switching device 39b to the second arrangement state (the retracted state).

Therefore, in the second observation mode, the second fluorescent drug is excited by second illumination light (second excitation light) emitted from the light guide 13. Therefore, the second fluorescence in the wavelength band of 790 to 850 nm and the reference light in the wavelength band of 790 to 810 nm are sequentially focused on the image pickup surface of the CCD 14 as return light from the observation target region 201.

If a determination result that the present time is not within the diagnosable time of the second fluorescent drug is obtained by the determining circuit 33d, even if the switching operation from another observation mode to the second observation mode is performed in the mode switching switch 15, the switching control circuit 33e of the control section 33 disables the switching operation by maintaining a control state of the motor 9 and the image pickup actuator control circuit 32 in a state before the switching operation is performed.

At a point when the determination result that the present time is within the diagnosable time of the second fluorescent drug is obtained by the determining circuit 33d, i.e., at a point when the present time reaches the diagnosis start time Ts of the second fluorescent drug, the switching control circuit 33e of the control section 33 may apply control for shifting the observation mode to the second observation mode to the motor 9 and the image pickup actuator control circuit 32 irrespective of an operation state of the mode switching switch 15.

If the determination result that the present time is not within the diagnosable time of the second fluorescent drug and the diagnosis end time Te of the second fluorescent drug elapses is obtained by the determining circuit 33d, the switching control circuit 33e of the control section 33 may disable the switching operation from another observation mode to the second observation mode and apply the control for switching the second observation mode to another observation mode (e.g., the fourth observation mode explained below) to the motor 9 and the image pickup actuator control circuit 32 irrespective of an operation state of the mode switching switch 15.

On the other hand, if the determination result that the present time is not within the diagnosable time of the second fluorescent drug is obtained by the determining circuit 33d, the notification signal generating circuit 61 generates a character signal for displaying a character string for informing that the present time is a time period when the switching to the second observation mode is impossible. The character signal includes a message that, for example, the present time does not reach the diagnosis start time Ts of the second fluorescent drug or the present time is after the diagnosis end time Te of the second fluorescent drug. The notification signal generating circuit 61 outputs the character signal to the monitor 4. Further, if the determination result that the present time is not within the diagnosable time of the second fluorescent drug is obtained by the determining circuit 33d, the notification signal generating circuit 61 generates a sound signal for generating sound for informing that the present time is a time period when the switching to the second observation mode is impossible. The sound signal includes a message that, for example, the present time does not reach the diagnosis start time Ts of the second fluorescent drug or the present time is after the diagnosis end time Te of the second fluorescent drug. The notification signal generating circuit 61 outputs the sound signal to the speaker 63.

If a determination result that the present time is within both the diagnosable times of the first and the second fluorescent drugs is obtained by the determining circuit 33d, when switching operation to a third observation mode for radiating excitation lights corresponding to the first and the second fluorescent drugs is performed in the mode switching switch 15 (or when switching from another observation mode to the third observation mode is performed irrespective of an operation state of the mode switching switch 15), the switching control circuit 33e of the control section 33 interposes the third excitation light filter 56 on the optical path of the lamp 7 by controlling the motor 9 of the light source device 1. Specifically, in the third observation mode, frame-sequential third illumination light including reference light in the wavelength band of 790 to 810 nm, the first excitation light in the wavelength band of 600 to 650 nm, and the second excitation light in the wavelength band of 700 to 760 nm is supplied to the light guide 13.

Further, if the determination result that the present time is within the both diagnosable times of the first and the second fluorescent drugs is obtained by the determining circuit 33d, when the switching operation to the third observation mode is performed in the mode switching switch 15 (or when switching from another observation mode to the third observation mode is performed irrespective of an operation state of the mode switching switch 15), the switching control circuit 33e of the control section 33 controls the image pickup actuator control circuit 32 to thereby cause the image pickup actuator 39 to operate to synchronize the timing when the optical filters 41, 42, and 43 are sequentially interposed on the optical path of the lamp 7, the switching timing of the arrangement state of the optical filter 117a in the filter switching device 39a, and the switching timing of the arrangement state of the optical filter 117b in the filter switching device 39b.

Figure 24:
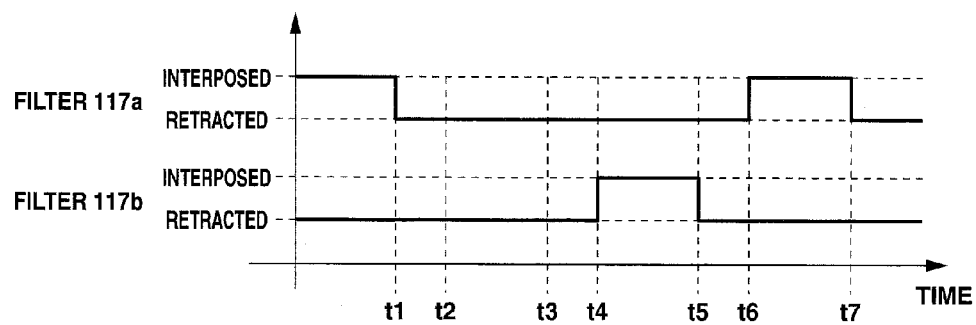
FIG. 24 is a timing chart showing interposing actions and retracting actions in a third observation mode of the respective optical filters provided in the image pickup actuator.

Specifically, as shown in FIGS. 17, 18, and 24, in the third observation mode, in the exposure period of the CCD 14 and the period in which the optical filter 41 is interposed on the optical path of the lamp 7, the image pickup actuator control circuit 32 sets the arrangement state of the optical filter 117a of the filter switching device 39a to the first arrangement state (the interposed state) and further sets the arrangement state of the optical filter 117b of the filter switching device 39b to the second arrangement state (the retracted state). As shown in FIGS. 17, 18, and 24, in the third observation mode, in the exposure period of the CCD 14 and the period in which the optical filter 43 is interposed on the optical path of the lamp 7, the image pickup actuator control circuit 32 sets the arrangement state of the optical filter 117a of the filter switching device 39a to the second arrangement state (the retracted state) and further sets the arrangement state of the optical filter 117b of the filter switching device 39b to the first arrangement state (the interposed state). On the other hand, as shown in FIGS. 17, 18, and 24, in the third observation mode, in the readout period of the CCD 14 or the period in which the optical filter 42 is interposed on the optical path of the lamp 7, the image pickup actuator control circuit 32 sets the arrangement state of the optical filter 117a of the filter switching device 39a to the second arrangement state (the retracted state) and further sets the arrangement state of the optical filter 117b of the filter switching device 39b to the second arrangement state (the retracted state).

Therefore, in the third observation mode, the first fluorescent drug and the second fluorescent drug are excited by third illumination light (the first excitation light and the second excitation light) emitted from the light guide 13. Therefore, the first fluorescence in the wavelength band of 680 to 750 nm, the second fluorescence in the wavelength band of 790 to 850 nm, and the reference light in the wavelength band of 790 to 810 nm are sequentially focused on the image pickup surface of the CCD 14 as return light from the observation target region 201.

If a determination result that the present time is not within both the diagnosable times of the first and the second fluorescent drugs is obtained by the determining circuit 33d, even if the switching operation from another observation mode to the third observation mode is performed in the mode switching switch 15, the switching control circuit 33e of the control section 33 disables the switching operation by maintaining a control state of the motor 9 and the image pickup actuator control circuit 32 in a state before the switching operation is performed.

On the other hand, if the determination result that the present time is not within both the diagnosable times of the first and the second fluorescent drugs is obtained by the determining circuit 33d, the notification signal generating circuit 61 generates a character signal for displaying a character string for informing that the present time is a time period when the switching to the third observation mode is impossible. The character signal includes a message that, for example, the present time does not reach both the diagnosis start times Ts of the first and the second fluorescent drugs or the present time is after both the diagnosis end times Te of the first and the second fluorescent drugs. The notification signal generating circuit 61 outputs the character signal to the monitor 4. Further, if the determination result that the present time is not within both the diagnosable times of the first and the second fluorescent drugs is obtained by the determining circuit 33d, the notification signal generating circuit 61 generates a sound signal for generating sound for informing that the present time is a time period when the switching to the third observation mode is impossible. The sound signal includes a message that, for example, the present time does not reach both the diagnosis start times Ts of the first and the second fluorescent drugs or the present time is after both the diagnosis end times Te of the first and the second fluorescent drugs. The notification signal generating circuit 61 outputs the sound signal to the speaker 63.

The notification signal generating circuit 61 may operate, based on a determination result of the determining circuit 33d, to perform notification at points when the present time reaches the diagnosis start time Ts and the diagnosis end time Te of the second fluorescent drug or may operate to cause the monitor 4 to always display the diagnosis start time Ts and the diagnosis end time Te of the second fluorescent drug.

If a determination result that the present time is within the diagnosable time of one fluorescent drug of the first and the second fluorescent drugs and the present time is not within diagnosable time of the other fluorescent drug is obtained by the determining circuit 33d, the switching control circuit 33e of the control section 33 disables the switching operation to the third observation mode and applies, to the motor 9 and the image pickup actuator control circuit 32, control for switching the observation mode to the observation mode corresponding to the one fluorescent drug (the first or the second observation mode).

If the determination result that the present time is within the diagnosable time of one fluorescent drug of the first and the second fluorescent drugs and the present time is not within diagnosable time of the other fluorescent drug is obtained by the determining circuit 33d, the notification signal generating circuit 61 generates a character signal for displaying a character string. The character signal includes a message that, for example, because the present time is outside the diagnosable time of the other fluorescent drug and the present time is a time period when switching to the third observation mode is impossible, the observation mode is switched to the observation mode corresponding to the one fluorescent drug. The notification signal generating circuit 61 outputs the character signal to the monitor 4. Further, a determination result that the present time is not within the diagnosable times of both the first and the second fluorescent drugs is obtained by the determining circuit 33d, the notification signal generating circuit 61 generates a sound signal for generating sound. The sound signal includes a message that, for example, because the present time is outside the diagnosable time of the other fluorescent drug and the present time is a time period when switching to the third observation mode is impossible, the observation mode is switched to the observation mode corresponding to the one fluorescent drug. The notification signal generating circuit 61 outputs the sound signal to the speaker 63.

After the present time passes a time period within the diagnosable time of the one fluorescent drug of the first and the second fluorescent drugs and not within the diagnosable time of the other fluorescent drug, at a point when the present time reaches time within both the diagnosable times of the first and the second fluorescent drug, the switching control circuit 33e of the control section 33 may apply, based on a determination result obtained by the determining circuit 33d, control for shifting the observation mode corresponding to the one fluorescent drug (the first or the second observation mode) to the third observation mode to the motor 9 and the image pickup actuator control circuit 32 irrespective of an operation state of the mode switching switch 15. After the present time passes a time period within the diagnosable time of the one fluorescent drug of the first and the second fluorescent drugs and not within the diagnosable time of the other fluorescent drug, when the present time enters a time period within both the diagnosable times of the first and the second fluorescent drug, the switching control circuit 33e of the control section 33 may apply, based on a determination result obtained by the determining circuit 33d, control for shifting the observation mode corresponding to the one fluorescent drug (the first or the second observation mode) to the third observation mode to the motor 9 and the image pickup actuator control circuit 32 when the switching operation to the third observation mode is performed in the mode switching switch 15.

On the other hand, if a determination result that the present time is not within the diagnosable time of at least one fluorescent drug of the first and the second fluorescent drugs is obtained by the determining circuit 33d, the switching control circuit 33e of the control section 33 may disable all the switching operations to the first to third observation modes and apply control for switching the observation mode to the fourth observation mode explained below to the motor 9 and the image pickup actuator control circuit 32. In such a case, the notification signal generating circuit 61 generates a character signal for displaying a character string. The character signal includes a message that, for example, since the present time is a time period when fluorescence observation is impossible, the observation mode is switched to the fourth observation mode. The notification signal generating circuit 61 outputs the character signal to the monitor 4. Further, the notification signal generating circuit 61 generates a sound signal for generating sound including the message and outputs the sound signal to the speaker 63.

When switching operation to the fourth observation mode for radiating white light is performed in the mode switching switch 15 (or when switching from another observation mode to the fourth observation mode is performed irrespective of an operation state of the mode switching switch 15), the switching control circuit 33e of the control section 33 interposes the normal light filter 50 on the optical path of the lamp 7 by controlling the motor 9 of the light source device 1. Specifically, in the fourth observation mode, frame-sequential fourth illumination light (white light) including red light (R light) in the wavelength band of 600 to 650 nm, green light (G light) in the wavelength band of 500 to 600 nm, and blue light (B light) in the wavelength band of 400 to 500 nm is supplied to the light guide 13.

Further, when the switching operation to the fourth observation mode is performed in the mode switching switch 15 (or when switching from another observation mode to the fourth observation mode is performed irrespective of an operation state of the mode switching switch 15), the switching control circuit 33e of the control section 33 controls the image pickup actuator control circuit 32 to thereby cause the image pickup actuator 39 to operate such that the arrangement state of the optical filter 117a of the filter switching device 39a and the arrangement state of the optical filter 117b of the filter switching device 39b change to the second arrangement state (the retracted state).

Therefore, in the fourth observation mode, reflected light of fourth illumination light (R light, G light, and B light) emitted from the light guide 13 is sequentially focused on the image pickup surface of the CCD 14 as return light from the observation target region 201.

On the other hand, after the control for switching the observation mode to the fourth observation mode is applied to the motor 9 and the image pickup actuator control circuit 32, if a determination result that $0 \leq T \leq Te$ is further obtained by the determining circuit 33d, the switching control circuit 33e of the control section 33 controls the light adjusting circuit 27 to increase an aperture amount of the aperture 12 to thereby emit the fourth illumination light from the light source device 1 in a state in which an intensity in at least a part of wavelength bands among the wavelength bands included in the fourth illumination light is reduced to a predetermined intensity.

Specifically, the light adjusting circuit 27 increases the aperture amount of the aperture 12 such that intensities in the wavelength bands of the fourth illumination light emitted from the light source device 1 are equal to or smaller than a predetermined value. In such a case, the light adjusting circuit 27 increases the amplification ratio of the amplification ratio control circuit 29 such that brightness of the reflected light of the fourth illumination light focused on the image pickup surface of the CCD 14 is suitable for observation.

The light adjusting circuit 27 relatively increases, based on a timing signal from the timing generator 30, the aperture amount of the aperture 12 at a timing when the R light, the wavelength band of which overlaps that of one of the first and second excitation lights, among the R light, the G light, and the B light to thereby reduce an intensity of the R light emitted from the light source device 1 to be equal to or smaller than a predetermined value. In such a case, the color balance correcting circuit 20 sets a color balance correction coefficient for making color balance of an observation image corresponding to the reflected light of the fourth illumination light suitable for observation (e.g., R:G:B=1:1:1) and performs adjustment of the color balance. The adjustment of the color balance involved in a decrease in the intensity (of the reflected light) of the R light is not limited to adjustment performed independently in the color balance correcting circuit 20 and may be adjustment performed by association of the color balance correcting circuit 20 and the tone adjusting circuit 24.

The aperture amount of the aperture 12 (the intensity of the fourth illumination light) controlled by the operation of the light adjusting circuit 27 in the fourth observation mode is a parameter set according to a discoloration characteristic of a fluorescent drug. One aperture amount may be able to be selected and set for each type of a fluorescent drug out of plural aperture amounts according to, for example, operation of the keyboard 62. The aperture amount may be stored in the storing circuit 33b in a state in which the aperture amount is set in advance for each type of the fluorescent drug.

On the other hand, according to this embodiment, for example, after applying the control for shifting the observation mode to the fourth observation mode to the image pickup actuator control circuit 32, if the determination result that $0 \leq T \leq Te$ is further obtained by the determining circuit 33d, the switching control circuit 33e of the control section 33 may apply control for switching the normal light filter 50 provided in the switching filter 8 to a not-shown filter for discoloration prevention to the motor 9 of the light source device 1.

Figure 25:
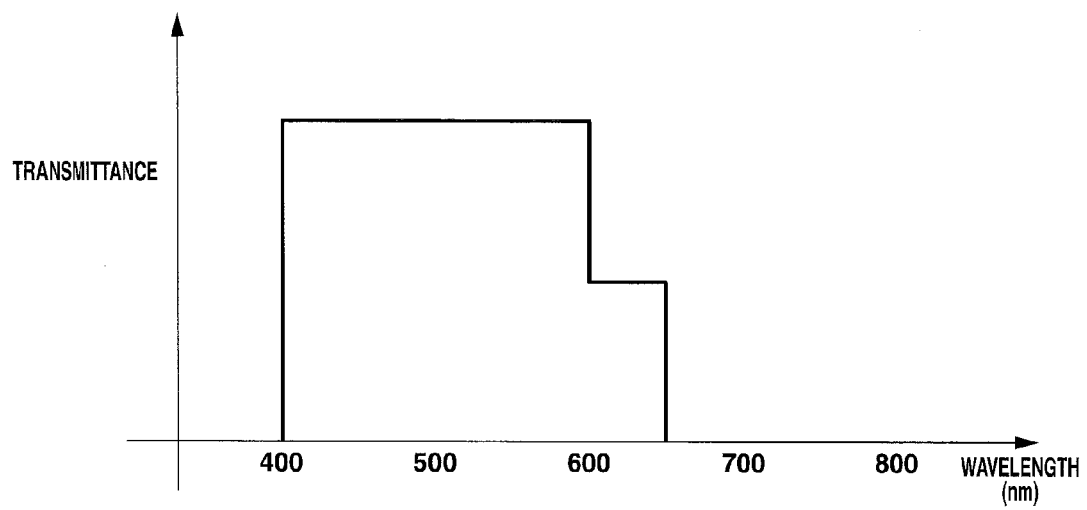
FIG. 25 is a graph showing an example of a discoloration preventing filter applicable in the first embodiment.
Figure 26:
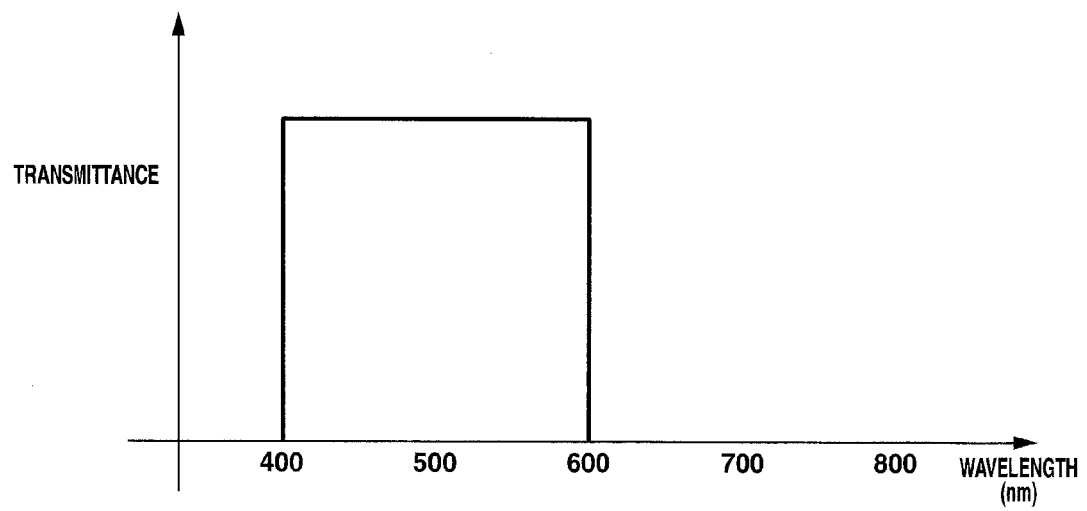
FIG. 26 is a graph showing an example of a discoloration preventing filter applicable in the first embodiment and different from the example shown in FIG. 25.

As the filter for discoloration prevention, for example, a filter including characteristics shown in FIGS. 25 and 26 configured to be capable of attenuating intensity of a wavelength band overlapping the first or the second excitation light among the wavelength bands included in the fourth illumination light to predetermined intensity can be applied.

FIG. 25 is a diagram showing an example of a filter for discoloration prevention applicable in the first embodiment. FIG. 26 is a diagram showing an example of a filter for discoloration prevention applicable in the first embodiment different from the filter for discoloration prevention shown in FIG. 25.

The filter for discoloration prevention formed to include the characteristic illustrated in FIG. 25 allows lights (the B light and the G light) in a wavelength band equal to or longer than 400 nm and shorter than 600 nm among the wavelength band included in the fourth illumination light to pass without generally attenuating the lights and attenuates the light (the R light) in a wavelength band equal to or longer than 600 nm and equal to or shorter than 650 nm to about half intensity and allows the light to pass. Therefore, when the filter for discoloration prevention is switched to the filter for discoloration prevention including the characteristic illustrated in FIG. 25, the color balance adjustment explained above is performed in the color balance correcting circuit 20 (and the tone adjusting circuit 24).

The filter for discoloration prevention formed to include the characteristic illustrated in FIG. 26 allows lights (the B light and the G light) in the wavelength band equal to or longer than 400 nm and shorter than 600 nm among the wavelength band included in the fourth illumination light to pass without generally attenuating the lights and blocks the light (the R light) in the wavelength band equal to or longer than 600 nm and equal to or shorter than 650 nm (attenuates intensity of the light to 0). Therefore, when the filter for discoloration prevention is switched to the filter for discoloration prevention including the characteristic illustrated in FIG. 26, processing for generating an observation image without using the reflected light of the R light is performed by the sections of the processor 3.

According to this embodiment, in the fourth observation mode, control for increasing the aperture amount of the aperture 12 and reducing the intensity of the R light and control for switching the filter for discoloration prevention to the filter for discoloration prevention illustrated in FIG. 25 and attenuating the intensity of the R light may be configured to be performed together.

As explained above, according to this embodiment, when fluorescence from the fluorescent drug administered to the observation target region of the subject is observed, it is possible to suppress, as much as possible, generation of fluorescence in time periods other than a time period when diagnosis of the observation target region can be performed. As a result, it is possible to improve diagnosability in performing the diagnosis of the observation target region.

Second Embodiment

FIGS. 27 to 32 are diagrams related to a second embodiment of the present invention.

In this embodiment, detailed explanation concerning components including configurations or the like same as those in the first embodiment is omitted as appropriate. Components having configurations or the like different from those in the first embodiment are mainly explained.

Figure 27:
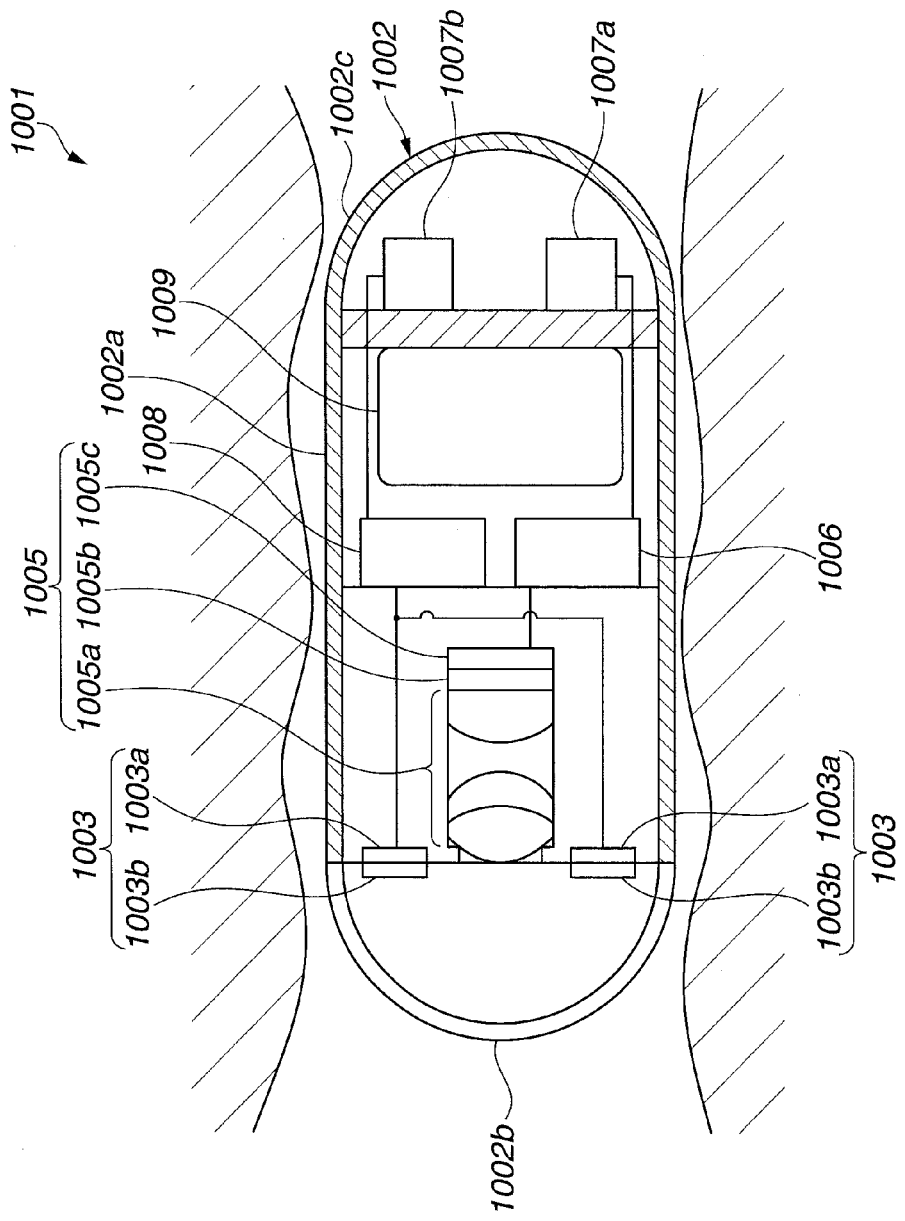
FIG. 27 is a diagram showing a configuration of a main part of a capsule-type medical apparatus according to a second embodiment of the present invention.
Figure 28:
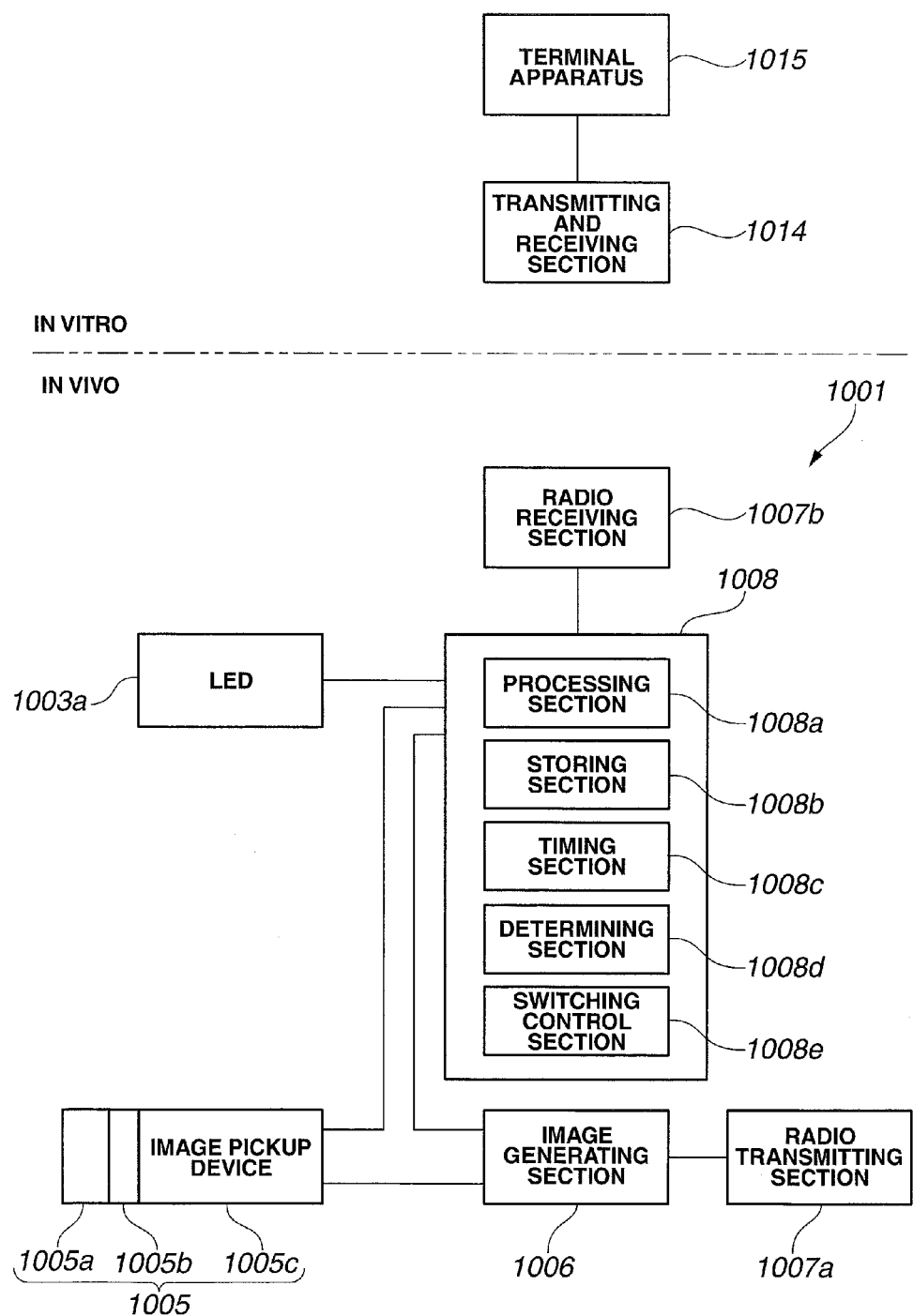
FIG. 28 is a block diagram showing a configuration of a main part of a capsule-type medical apparatus system including the capsule-type medical apparatus shown in FIG. 27.

FIG. 27 is a diagram showing a configuration of a main part of a capsule-type medical apparatus in the second embodiment of the present invention. FIG. 28 is a block diagram showing a configuration of a main part of a capsule-type medical apparatus system including the capsule-type medical apparatus shown in FIG. 27. In FIG. 27, for simplification, wires from a battery 1009 to sections of a capsule-type medical apparatus 1001 are omitted. In FIG. 28, for simplification, a part of a configuration of the capsule-type medical apparatus 1001 is omitted.

The capsule-type medical apparatus 1001 includes, as shown in FIGS. 27 and 28, a capsule-type housing 1002, excitation light emitting sections 1003 that are housed in the housing 1002 and radiate excitation light via a transparent window 1002b, an image pickup section 1005 that picks up an image of an observation target region in a body cavity and outputs an image pickup signal, an image generating section 1006 that applies various kinds of image processings to the image pickup signal outputted from the image pickup section 1005 and generates an image signal, a radio transmitting section 1007a that can transit a radio signal to an outside of the housing 1002, a radio receiving section 1007b that can receive a radio signal transmitted from the outside of the housing 1002, a control section 1008 that performs control for the sections of the capsule-type medical apparatus 1001, and the battery 1009 that can supply driving power for driving the sections of the capsule-type medical apparatus 1001.

As shown in FIG. 28, on an outside of the capsule-type medical apparatus 1001, a transmitting and receiving section 1014 that can transmit and receive a radio signal between the radio transmitting sections 1007a and the radio receiving section 1007b and a terminal apparatus 1015 that can perform bidirectional communication with the transmitting and receiving section 1014 are provided. In other words, the capsule-type medical apparatus system according to this embodiment includes, as shown in FIG. 28, the capsule-type medical apparatus 1001, the transmitting and receiving section 1014, and the terminal apparatus 1015.

The capsule-type housing 1002 is formed by sealing both ends of a cylindrical housing main body 1002a with the transparent window 1002b and an end plate 1002c having a semispherical shape.

The excitation light emitting sections 1003 include LEDs 1003a that emit light in a wavelength band same as the wavelength band of the lamp 7 and excitation light filters 1003b arranged in front of light emitting surfaces of the LEDs 1003a and formed to have a characteristic same as the characteristic of the first excitation light filter 51 (see FIG. 10).

Figure 29:
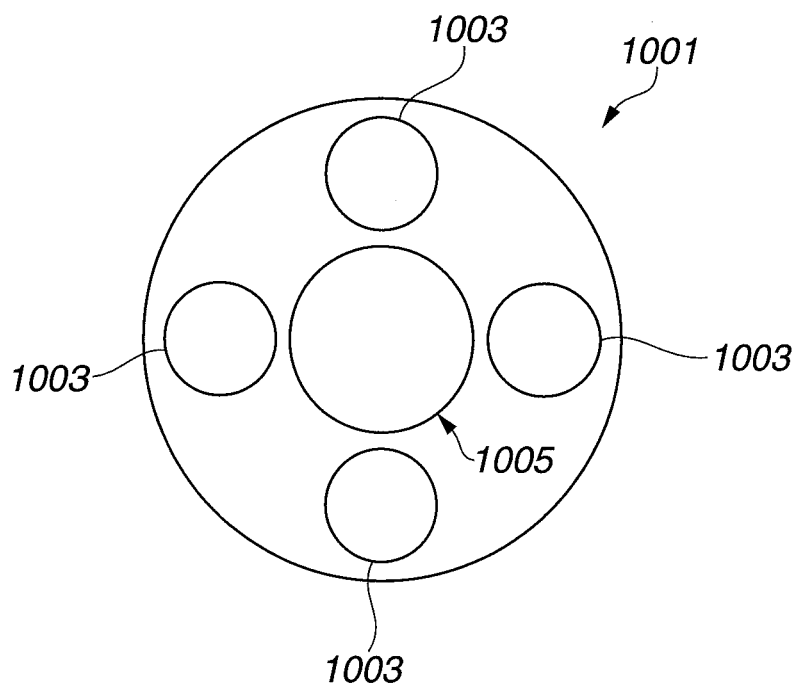
FIG. 29 is a diagram showing an example of positions where excitation light emitting sections and an image pickup section are arranged in the capsule-type medical apparatus shown in FIG. 27.

FIG. 29 is a diagram showing an example of positions where the excitation light emitting sections and the image pickup section are arranged in the capsule-type medical apparatus shown in FIG. 27.

For example, as shown in FIG. 29, the excitation light emitting sections 1003 of the capsule-type medical apparatus 1001 are not limited to four excitation light emitting sections 1003 arranged around the image pickup section 1005. Any number of excitation light emitting sections 1003 may be arranged around the image pickup section 1005 as long as the number is equal to or larger than one.

The image pickup section 1005 includes an object optical system 1005a that condenses return light made incident on an inside of the housing 1002 via the transparent window 1002b, an excitation light cut filter 1005b formed to have a characteristic same as the characteristic of the optical filter 117a (see FIG. 6), and an image pickup device 1005c such as a high-sensitivity CCD that can pick up an image of light passed through the object optical system 1005a and the excitation light cut filter 1005b and output an image pickup signal.

The radio transmitting section 1007a is configured to be capable of applying signal processing such as modulation to an image signal generated by the image generating section 1006 to thereby generate a radio signal and transmit the generated radio signal to the transmitting and receiving section 1014.

The radio receiving section 1007b is configured to be capable of receiving a radio signal transmitted from the transmitting and receiving section 1014 and outputting data obtained by applying signal processing such as demodulation to the radio signal to the control section 1008.

The control section 1008 including a CPU and a memory includes a processing section 1008a equivalent to the processing circuit 33a in the first embodiment, a storing section 1008b equivalent to the storing circuit 33b in the first embodiment, a timing section 1008c equivalent to the timing circuit 33c in the first embodiment, a determining section 1008d equivalent to the determining circuit 33d in the first embodiment, and a switching control section 1008e equivalent to the switching control circuit 33e in the first embodiment. (The switching control section 1008e of) the control section 1008 causes the sections to operate based on data outputted from the radio receiving section 1007b to thereby apply control explained below to the sections of the capsule-type medical apparatus 1001.

The terminal apparatus 1015 is configured as a personal computer, a portable terminal, or the like that can perform bidirectional communication with the transmitting and receiving section 1014. The terminal apparatus 1015 includes, for example, a terminal apparatus main body including a recording medium for recording an image corresponding to an output signal from the transmitting and receiving section 1014, a display section that can display an image or the like corresponding to the output signal from the transmitting and receiving section 1014, and an input operation section that can perform, for example, input operation of a character string.

Action of the capsule-type medical apparatus 1001 according to this embodiment is explained below.

First, after turning on a power supply for the capsule-type medical apparatus 1001, the surgeon or the like substantially simultaneously performs administration of a fluorescent drug to an observation target region of a subject and leading of the capsule-type medical apparatus 1001 into the subject.

Subsequently, the surgeon or the like operates an input operation section of the terminal apparatus 1015 to thereby input various kinds of information such as the reference values Ns and Ne, a type of a fluorescent drug in use, an organ to which a target region to which the fluorescent drug is administered (the observation target region) belongs, a method of administering the fluorescent drug to the target region, and start time of the administration of the fluorescent drug to the subject.

When the terminal apparatus main body of the terminal apparatus 1015 detects that the respective pieces of information are inputted in the input operation section, after converting the inputted information into digital data, the terminal apparatus main body operates to cause the transmitting and receiving section 1014 to transmit a radio signal including the converted digital data to the radio receiving section 1007b.

On the other hand, when the control section 1008 detects that new reference values Ns and Ne are set, the control section 1008 updates the reference values Ns and Ne stored in the storing section 1008b based on the digital data outputted from the radio receiving section 1007b.

After selecting, based on the digital data outputted from the radio receiving section 1007b, one table data coinciding with a type of a fluorescent drug in use out of plural table data of fluorescent drugs stored in the storing section 1008b, the control section 1008 further selects, out of the selected one table data, one drug kinetics corresponding to a combination of the organ to which the target region to which the fluorescent drug is administered (the observation target region) belongs and the method of administering the fluorescent drug to the target region.

According to this embodiment, for example, the reference values Ns and Ne are set in advance for each of drug kinetics in the respective table data stored in the storing section 1008b, whereby the reference values Ns and Ne may be uniquely determined according to selection of one drug kinetics.

The processing section 1008a of the control section 1008 matches, based on the reference values Ns and Ne stored in the storing section 1008b and the start time of administration of the fluorescent drug to the subject, a point of elapsed time T=0 from the administration of the fluorescent drug to the subject and an accumulation amount N=0 of the fluorescent drug to the start time of the administration in the one drug kinetics selected by the processing, acquires the diagnosis start time Ts equivalent to the first elapsed time T when the accumulation amount N=Ns, and further acquires the diagnosis end time Te equivalent to the elapsed time T when the accumulation amount N=Ne last after the diagnosis start time Ts.

The determining section 1008d of the control section 1008 performs, at any time, based on the diagnosis start time Ts and the diagnosis end time Te acquired by the processing section 1008a and a measurement result of the timing section 1008c, determination concerning whether present time is equivalent to time within diagnosable time, which is a time period from the diagnosis start time Ts to the diagnosis end time Te.

If a determination result that the present time is not within the diagnosable time is obtained by the determining section 1008d, the switching control section 1008e of the control section 1008 performs control for causing the LEDs 1003a of the excitation light emitting sections 1003 to extinguish light, performs control for stopping driving of the image pickup device 1005c of the image pickup section 1005, and further performs control for stopping operations of the image generating section 1006 and the radio transmitting section 1007a.

If a determination result that the present time is within the diagnosable time is obtained by the determining section 1008d, the switching control section 1008e of the control section 1008 performs control for causing the LEDs 1003a of the excitation light emitting sections 1003 to emit light, performs control for driving the image pickup device 1005c of the image pickup section 1005, and further performs control for causing the image generating section 1006 and the radio transmitting section 1007a to operate.

Specifically, with the capsule-type medical apparatus 1001 according to this embodiment, when the present time does not reach the diagnosis start time Ts of the fluorescent drug administered to the subject and when the present time is after the diagnosis end time Te of the fluorescent drug administered to the subject, respective operations concerning generation of excitation light, output an image pickup signal, image processing related to generation of an image signal, and transmission of a radio signal are not performed. With the capsule-type medical apparatus 1001 according to this embodiment, only when the present time belongs to a time period from the diagnosis start time Ts to the diagnosis end time Te, the respective operations concerning the generation of excitation light, the output of an image pickup signal, the image processing related to generation of an image signal, and the transmission of a radio signal are performed.

Figure 30:
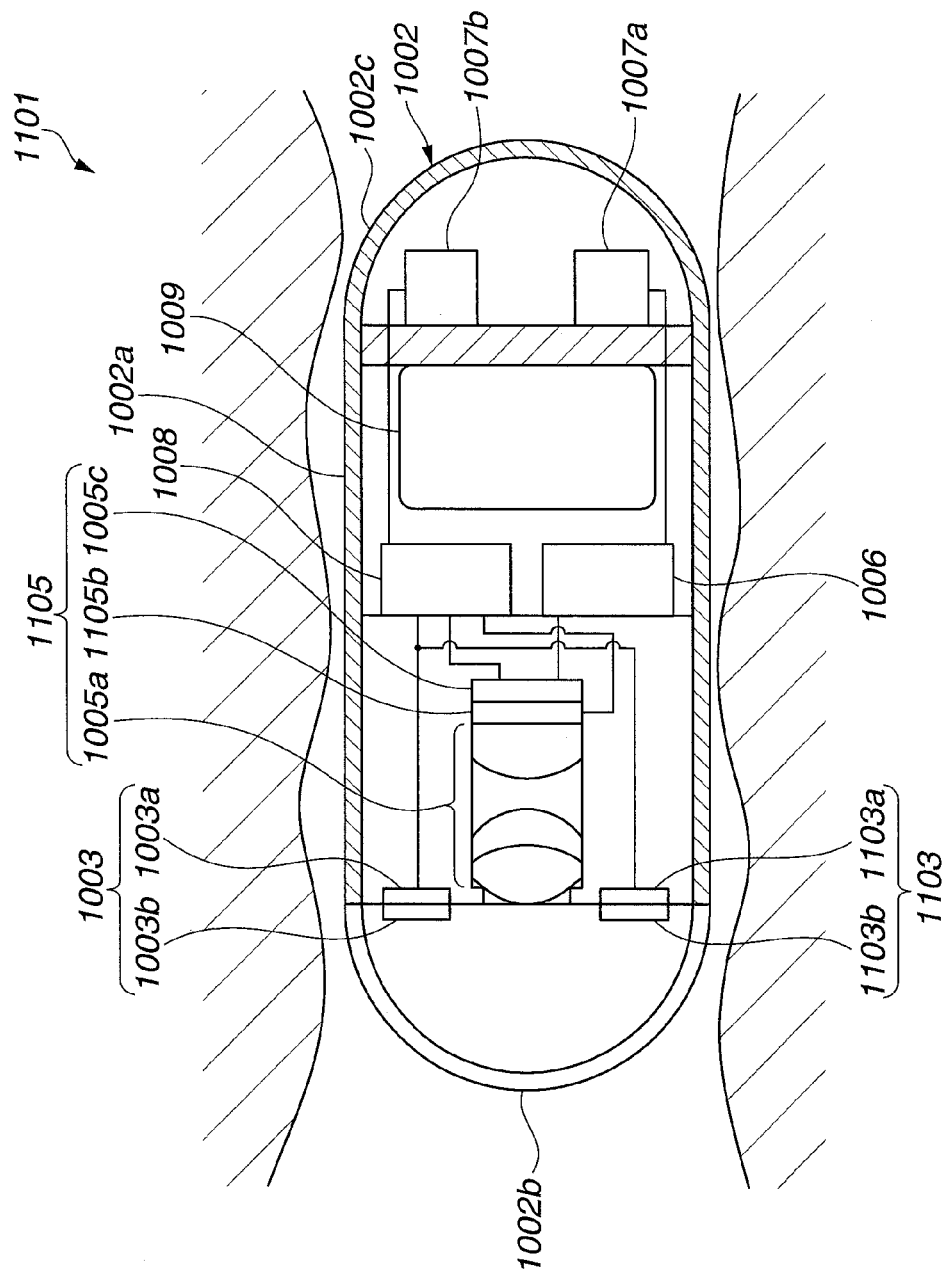
FIG. 30 is a diagram showing a configuration of a main part of a capsule-type medical apparatus according to a modification of the second embodiment of the present invention.

On the other hand, according to this embodiment, a capsule-type medical apparatus system may be configured using a capsule-type medical apparatus 1101 shown in FIG. 30 instead of using the capsule-type medical apparatus 1001 illustrated in FIG. 27.

Figure 31:
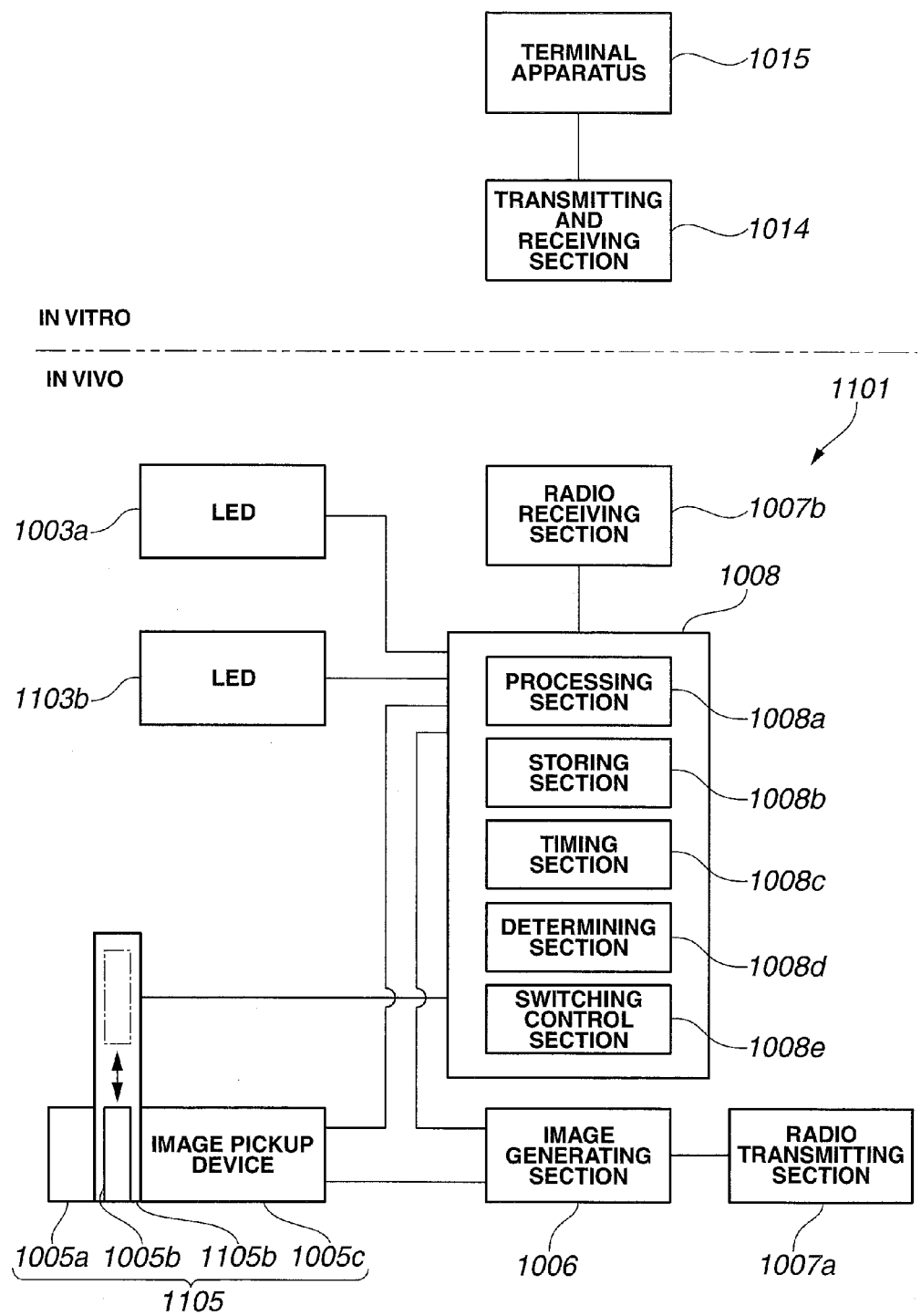
FIG. 31 is a block diagram showing a configuration of a main part of a capsule-type medical apparatus system including the capsule-type medical apparatus shown in FIG. 30.

FIG. 30 is a diagram showing a configuration of a main part of a capsule-type medical apparatus according to a modification of the second embodiment of the present invention. FIG. 31 is a block diagram showing a configuration of a main part of a capsule-type medical apparatus system including the capsule-type medical apparatus shown in FIG. 30. In FIG. 30, for simplification, wires from the battery 1009 to respective sections of the capsule-type medical apparatus 1101 are omitted. In FIG. 31, for simplification, a part of a configuration of the capsule-type medical apparatus 1101 is omitted.

The capsule-type medical apparatus 1101 includes, as shown in FIGS. 30 and 31, the housing 1002, the excitation light emitting sections 1003, white light emitting sections 1103 that are housed in the housing 1002 and radiate white light via the transparent window 1002b, the image pickup section 1105, the image generating section 1006, the radio transmitting section 1007a, the radio receiving section 1007b, the control section 1008, and the battery 1009.

As shown in FIG. 31, on an outside of the capsule-type medical apparatus 1101, the transmitting and receiving section 1014 that can transmit and receive a radio signal between the radio transmitting sections 1007a and the radio receiving section 1007b and the terminal apparatus 1015 that can perform bidirectional communication with the transmitting and receiving section 1014 are provided. In other words, the capsule-type medical apparatus system according to the modification of this embodiment includes, as shown in FIG. 31, the capsule-type medical apparatus 1101, the transmitting and receiving section 1014, and the terminal apparatus 1015.

The white light emitting sections 1103 include LEDs 1103a that emit light in a wavelength band same as the wavelength band of the lamp 7 and white light filters 1103b arranged in front of light emitting surfaces of the LEDs 1103a and formed to have a characteristic same as the characteristic of the normal light filter 50 (see FIG. 9).

Figure 32:
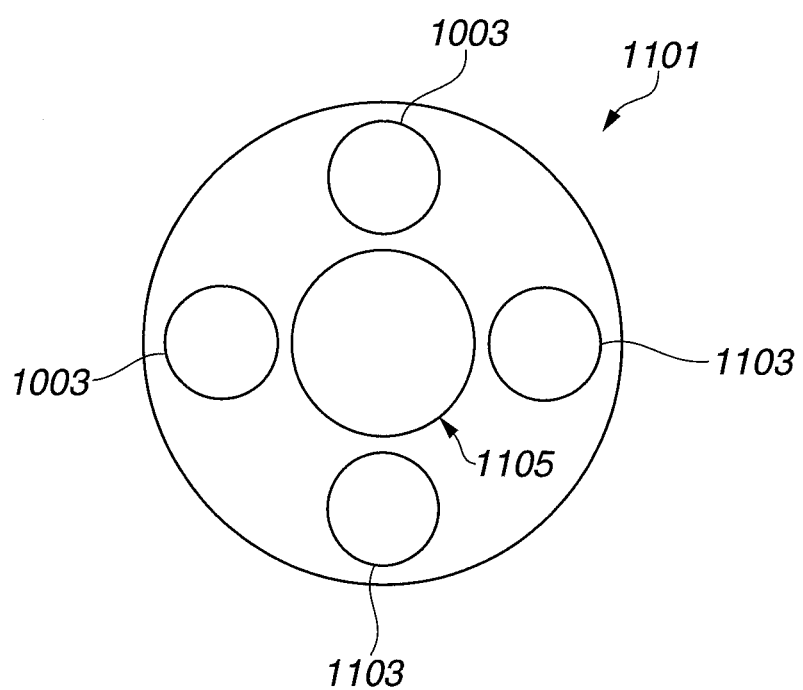
FIG. 32 is a diagram showing an example of positions where excitation light emitting sections, white light emitting sections, and an image pickup section are arranged in the capsule-type medical apparatus shown in FIG. 30.

FIG. 32 is a diagram showing an example of positions where the excitation light illuminating sections, the white light emitting sections, and the image pickup section are arranged in the capsule-type medical apparatus shown in FIG. 30.

The excitation light emitting sections 1003 and the white light emitting sections 1103 of the capsule-type medical apparatus 1101 are not limited to two excitation light emitting sections 1003 and two white light emitting sections 1103 arranged around an image pickup section 1105, for example, as shown in FIG. 32. Any number of excitation light emitting sections 1003 and white light emitting sections 1103 may be arranged around the image pickup section 1105 as long as the number is equal to or larger than one.

The image pickup section 1105 includes the object optical system 1005a, the image pickup device 1005c, and a filter switching section 1105b arranged on an optical path between the object optical system 1005a and the image pickup device 1005c.

For example, as shown in FIG. 31, the filter switching section 1105b has a configuration capable of switching, according to control by the control section 1008, a state in which the excitation light cut filter 1005b is interposed on an optical path extending from the object optical system 1005a to the image pickup device 1005c and a state in which the excitation light cut filter 1005b is retracted from the optical path extending from the object optical system 1005a to the image pickup device 1005c.

In other words, the image pickup section 1105 is configured to be capable of focusing light passed through the object optical system 1005a and the excitation light cut filter 1005b on the image pickup device 1005c in a state in which the excitation light cut filter 1005b of the filter switching section 1105b is interposed on the optical path extending from the object optical system 1005a to the image pickup device 1005c. Further, the image pickup section 1105 is configured to be capable of focusing light passed through the object optical system 1005a on the image pickup device 1005c in a state in which the excitation light cut filter 1005b of the filter switching section 1105b is retraced from the optical path extending from the object optical system 1005a to the image pickup device 1005c.

The filter switching section 1105b of the image pickup section 1105 may include, for example, a configuration same as the configuration of the filter switching device 39a explained in the first embodiment. Further, the filter switching section 1105b may include other configurations as long as the filter switching section 1105b includes a configuration capable of switching the two states.

Action of the capsule-type medical apparatus 1101 according to the modification of this embodiment is explained below.

First, after turning on a power supply for the capsule-type medical apparatus 1101, the surgeon or the like substantially simultaneously performs administration of a fluorescent drug to a subject and leading of the capsule-type medical apparatus 1101 into the subject.

Subsequently, the surgeon or the like operates an input operation section of the terminal apparatus 1015 to thereby input respective kinds of information such as the reference values Ns and Ne, a type of a fluorescent drug in use, an organ to which a target region to which the fluorescent drug is administered (the observation target region) belongs, a method of administering the fluorescent drug to the target region, and start time of the administration of the fluorescent drug to the subject.

When the terminal apparatus main body of the terminal apparatus 1015 detects that the respective pieces of information are inputted in the input operation section, after converting the inputted information into digital data, the terminal apparatus main body operates to cause the transmitting and receiving section 1014 to transmit a radio signal including the converted digital data to the radio receiving section 1007b.

On the other hand, when the control section 1008 detects that new reference values Ns and Ne are set, the control section 1008 updates the reference values Ns and Ne stored in the storing section 1008b based on the digital data outputted from the radio receiving section 1007b.

After selecting, based on the digital data outputted from the radio receiving section 1007b, one table data coinciding with a type of a fluorescent drug in use out of plural table data of fluorescent drugs stored in the storing section 1008b, the control section 1008 further selects, out of the selected one table data, one drug kinetics corresponding to a combination of the organ to which the target region to which the fluorescent drug is administered (the observation target region) belongs and the method of administering the fluorescent drug to the target region.

The processing section 1008a of the control section 1008 matches, based on the reference values Ns and Ne stored in the storing circuit 1008b and the start time of administration of the fluorescent drug to the subject, a point of elapsed time T=0 from the administration of the fluorescent drug to the subject and an accumulation amount N=0 of the fluorescent drug to the start time of the administration in the one drug kinetics selected by the processing, acquires the diagnosis start time Ts equivalent to the first elapsed time T when the accumulation amount N=Ns, and further acquires the diagnosis end time Te equivalent to the elapsed time T when the accumulation amount N=Ne last after the diagnosis start time Ts.

The determining section 1008*d* of the control section 1008 performs, at any time, based on the diagnosis start time Ts and the diagnosis end time Te acquired by the processing section 1008*a* and a measurement result of the timing section 1008*c*, determination concerning whether present time is equivalent to time within diagnosable time, which is a time period from the diagnosis start time Ts to the diagnosis end time Te.

If a determination result that the present time is not within the diagnosable time is obtained by the determining section 1008*d*, the switching control section 1008*e* of the control section 1008 performs control for causing the LEDs 1003*a* of the excitation light emitting sections 1003 to extinguish light and performs control for causing the LEDs 1103*a* of the white light emitting section 1103 to emit light. The switching control section 1008*e* further applies, to the filter switching section 1105*b*, control for retracting the excitation light cut filter 1005*b* from the optical path extending from the object optical system 1005*a* to the image pickup device 1005*c*.

If a determination result that the present time is within the diagnosable time is obtained by the determining section 1008*d*, the switching control section 1008*e* of the control section 1008 performs control for causing the LEDs 1003*a* of the excitation light emitting sections 1003 to emit light and performs control for causing the LEDs 1103*a* of the white light emitting sections 1103 to extinguish light. The switching control section 1008*e* further applies, to the filter switching section 1105*b*, control for interposing the excitation light cut filter 1005*b* on the optical path extending from the object optical system 1005*a* to the image pickup device 1005*c*.

Specifically, with the capsule-type medical apparatus 1101 according to the modification of this embodiment, when the present time does not reach the diagnosis start time Ts of the fluorescent drug administered to the subject and when the present time is after the diagnosis end time Te of the fluorescent drug administered to the subject, white light is radiated, a white light image obtained by picking up an image of return light (reflected light) of the white light is acquired, and the white light image is transmitted by radio. With the capsule-type medical apparatus 1101 according to this embodiment, when the present time belongs to a time period from the diagnosis start time Ts to the diagnosis end time Te, radiation of excitation light is performed, a fluorescence image obtained by picking up an image of fluorescence excited by the excitation light is acquired, and the fluorescence image is transmitted by radio.

In the capsule-type medical apparatus 1101, for example, a filter for discoloration prevention having the characteristic shown in FIG. 25 may be provided instead of the white light filter 1103*b*, whereby intensity of a wavelength band overlapping a wavelength band of excitation light emitted from the excitation light emitting sections 1003 among the wavelength bands of the white light emitted from the white light emitting section 1103 may be attenuated to a predetermined intensity and the image generating section 1106 may perform adjustment of color balance for correcting the attenuation of such intensity.

In the capsule-type medical apparatus 1101, for example, when the image pickup device 1005*c* including a charge amplifying device is used, the control section 1008 (the switching control section 1008*e*) may perform control for changing a driving current of the LEDs 1103*a* to reduce an intensity of the respective wavelength bands of the white light emitted from the white light emitting section 1103 to a predetermined intensity and control for setting an amplification ratio of the charge amplifying device to an amplification ratio that can supplement such a reduction in the intensity.

As explained above, according to this embodiment, when fluorescence from the fluorescent drug administered to the observation target region of the subject is observed, it is possible to suppress, as much as possible, generation of fluorescence in a time period other than a time period when diagnosis of the observation target region is possible. As a result, it is possible to improve diagnosability in performing diagnosis of the observation target region.

The present invention is not limited to the embodiments explained above. It goes without saying that various alternations and applications are possible without departing from the spirit of the present invention.

What is claimed is:

1. A medical apparatus comprising:
   a storing section configured to store a drug kinetics in a living body in advance for each of plural kinds of fluorescent drugs;
   a processing section configured to acquire diagnosis start time based on the drug kinetics stored in the storing section, a target region of an object to be examined to which a desired fluorescent drug is administered, a method of administering the desired fluorescent drug to the target region, and administration start time of the desired fluorescent drug, the diagnosis start time being a first time when an accumulation amount of the desired fluorescent drug administered to the target region reaches a predetermined reference value after the administration start time;
   a determining section configured to determine whether present time reaches the diagnosis start time, based on the diagnosis start time acquired by the processing section; and
   a light source control section configured to perform control to a stop radiation of excitation light for exciting the desired fluorescent drug when the determining section determines that the present time does not reach the diagnosis start time and perform control to radiate the excitation light when the determining section determines that the present time reaches the diagnosis start time.

2. The medical apparatus according to claim 1, further comprising a timing section configured to measure elapsed time from the administration start time,
   wherein the determining section is configured to determine whether the present time reaches the diagnosis start time, based on the diagnosis start time acquired by the processing section and the elapsed time measured by the riming section.

3. The medical apparatus according to claim 1, wherein the storing section is configured to store the accumulation amount of a fluorescent drug in the target region of the object to be examined, which corresponds to elapsed time after the administration of the fluorescent drug into the object to be examined, section for each of the plural kinds of fluorescent drugs as the drug kinetics.

4. A medical apparatus comprising:
   a storing section configured to store a drug kinetics in a living body in advance for each of plural kinds of fluorescent drugs;

a processing section configured to acquire diagnosis start time based on the drug kinetics stored in the storing section, a target region of an object to be examined to which a desired fluorescent drug is administered, a method of administering the desired fluorescent drug to the target region, and administration start time of the desired fluorescent drug, the diagnosis start time being a first time when an accumulation amount of the desired fluorescent drug administered to the target region reaches a predetermined reference value after the administration start time;

a determining section configured to determine whether present time reaches the diagnosis start time, based on the diagnosis start time acquired by the processing section; and a light source control section configured to perform control to stop radiation of excitation light for exciting the desired fluorescent drug while radiating white light from a light emitting section, which can switch and emit the excitation light and the white light, when the determining section determines that the present time does not reach the diagnosis start time, and perform control to radiate the excitation light, when the determining section determines that the present time reaches the diagnosis start time.

5. The medical apparatus according to claim 4, further comprising a light intensity adjusting section configured to reduce an intensity of a wavelength band overlapping a wavelength band of the excitation light among wavelength bands of the white light when the determining section determines that the present time does not reach the diagnosis start time.

6. The medical apparatus according to claim 4, wherein a filter configured to attenuate intensity of a wavelength band overlapping a wavelength band of the excitation light among wavelength bands of the white light is provided in the light emitting section.

7. The medical apparatus according to claim 4, wherein:

the processing section is configured to acquire diagnosis end time, based on the drug kinetics stored in the storing section, the target region of the object to be examined to which the desired fluorescent drug is administered, the method of administering the desired fluorescent drug to the target region, and the administration start time of the desired fluorescent drug, the diagnosis end time being a last time when the accumulation amount of the desired fluorescent drug administered to the target region reaches the predetermined reference value after the diagnosis start time, the determining section is configured to determine whether the present time reaches the diagnosis end time, based on the diagnosis end time acquired by the processing section, and the light source control section is configured to perform control to radiate the white light from the light emitting section when the determining section determines that the present time reaches the diagnosis end time.

8. The medical apparatus according to claim 4, further comprising a notifying section configured to, if a determination result that the present time does not reach the diagnosis start time is obtained from the determining section, generate and output a message for notifying the determination result using at least one of visual information and auditory information.

* * * * *

UNITED STATES PATENT AND TRADEMARK OFFICE
CERTIFICATE OF CORRECTION

PATENT NO. : 8,868,160 B2
APPLICATION NO. : 13/495059
DATED : October 21, 2014
INVENTOR(S) : Kei Kubo et al.

It is certified that error appears in the above-identified patent and that said Letters Patent is hereby corrected as shown below:

Claims

Column 30, line 62 (Claim 3, line 6): should read: examined, for each of the plural kinds of fluorescent Signed and Sealed this
Third Day of November, 2015

Michelle K. Lee
*Director of the United States Patent and Trademark Office*